(12) United States Patent
Kim

(10) Patent No.: US 7,732,613 B2
(45) Date of Patent: Jun. 8, 2010

(54) MET KINASE INHIBITORS

(75) Inventor: Kyoung S. Kim, North Brunswick, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 859 days.

(21) Appl. No.: 11/520,520

(22) Filed: Sep. 13, 2006

(65) Prior Publication Data
US 2007/0060613 A1    Mar. 15, 2007

Related U.S. Application Data

(60) Provisional application No. 60/716,864, filed on Sep. 14, 2005.

(51) Int. Cl.
*C07D 215/38*    (2006.01)
(52) U.S. Cl. ........................................ 546/159; 546/153
(58) Field of Classification Search .................. 546/153, 546/159
See application file for complete search history.

(56) References Cited

U.S. PATENT DOCUMENTS

| 6,214,344 | B1 | 4/2001 | Schwall et al. |
| 6,268,379 | B1 | 7/2001 | Xue et al. |
| 6,429,213 | B1 | 8/2002 | Xue et al. |
| 6,828,320 | B2 | 12/2004 | Cockerill et al. |
| 6,858,626 | B2 | 2/2005 | Xue et al. |
| 2005/0288290 | A1 | 12/2005 | Borzilleri et al. |
| 2006/0004006 | A1 | 1/2006 | Borzilleri et al. |

FOREIGN PATENT DOCUMENTS

| WO | WO01/21594 | 3/2001 |
| WO | WO01/21596 | 3/2001 |
| WO | WO01/77085 | 10/2001 |
| WO | WO2004/018430 | 3/2004 |
| WO | WO2005/030140 | 4/2005 |

OTHER PUBLICATIONS

Bardelli, A. et al., "Concomitant activation of pathways downstream of Grb2 and PI 3-kinase is required for *MET*-mediated metastasis", Oncogene, vol. 18, pp. 1139-1146 (1999).
Bottaro, D. et al., "Identification of the Hepatocyte Growth Factor Receptor as the c-*met* Proto-Oncogene Product", Science, vol. 251, pp. 802-804 (1991).
Bussolino, F. et al., "Hepatocyte Growth Factor is a Potent Angiogenic Factor which Stimulates Endothelial Cell Motility and Growth", The J. of Cell Biology, vol. 119(3), pp. 629-641 (1992).
Camp, R. et al., "*Met* Expression is Associated with Poor Outcome in Patients with Axillary Lymph Node Negative Breast Carcinoma", Cancer, vol. 86(11), pp. 2259-2265 (1999).

(Continued)

*Primary Examiner*—D. Margaret Seaman
(74) *Attorney, Agent, or Firm*—Gary D. Greenblatt; Maureen S. Gibbons

(57) ABSTRACT

The present invention is directed to compounds that are useful for treating cancer having one of the following Formulas:

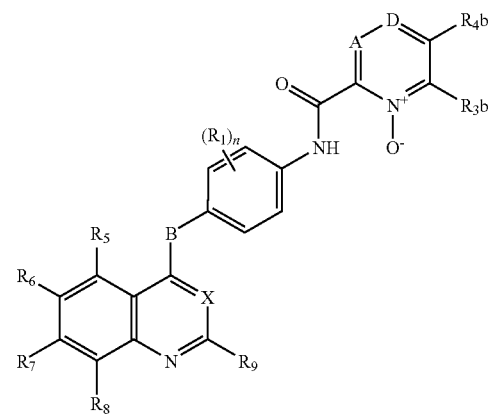

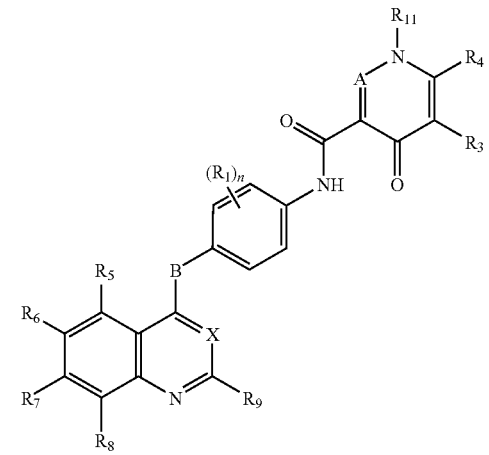

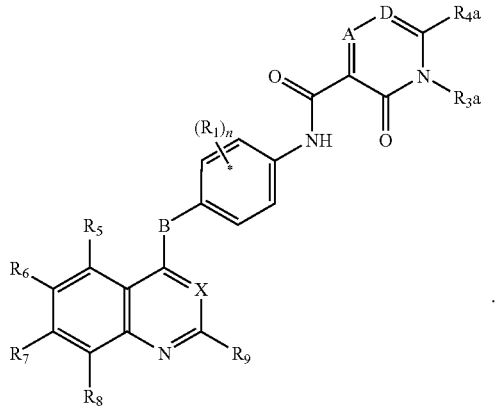

11 Claims, No Drawings

OTHER PUBLICATIONS

Cañibano, V. et al., "Mild Regioselective Halogenation of Activated Pyridines with N-Bromosuccinimide", Synthesis, vol. 14, pp. 2175-2179 (2001).

Christensen, J. et al., "A Selective Small Molecule Inhibitor of c-Met Kinase Inhibits c-Met-Dependent Phenotypes in Vitro and Exhibits Cytoreductive Antitumor Activity in Vivo", Cancer Research, vol. 63, pp. 7345-7355 (2003).

Cooper, C. et al., "Amplification and overexpression of the *met* gene in spontaneously transformed NIH3T3 mouse fibroblasts", The EMBO Journal, vol. 5(10), pp. 2623-2628 (1986).

Di Renzo, M. et al., "Overexpression and Amplification of the Met/HGF Receptor Gene during the Progression of Colorectal Cancer", Clinical Cancer Research, vol. 1, pp. 147-154 (1995).

Furge, K. et al., "Met receptor tyrosine kinase: enhanced signaling through adapter proteins", Oncogene, vol. 19, pp. 5582-5589 (2000).

Gual, P. et al., "Sustained recruitment of phospholipase C-γ to Gab1 is required for HGF-induced branching tubulogenesis", Oncogene, vol. 19, pp. 1509-1518 (2000).

Jiang, W. et al., "Reduction of Stromal Fibroblast-induced Mammary Tumor Growth, by Retroviral Ribozyme Transgenes to Hepatocyte Growth Factor/Scatter Factor and its Receptor, c-MET", Clinical Cancer Research, vol. 9, pp. 4274-4281 (2003).

Kenworthy, P. et al., "The presence of scatter factor in patients with metastatic spread to the pleura", Br. J. Cancer, vol. 66, pp. 243-247 (1992).

Kubo, K. et al., "Novel Potent Orally Active Selective VEGFR-2 Tyrosine Kinase Inhibitors: Synthesis, Structure-Activity Relationships, and Antitumor Activities of N-Phenyl-N'-{4-(4-quinolyloxy)phenyl} ureas", J. Med. Chem., vol. 48, pp. 1359-1366 (2005).

Lai, J. et al., "Involvement of Focal Adhesion Kinase in Hepatocyte Growth Factor-induced Scatter of Madin-Darby Canine Kidney Cells", The J. of Biological Chemistry, vol. 275(11), pp. 7474-7480 (2000).

Lee, J. et al., "A novel germ line juxtamembrane Met mutation in human gastric cancer", Oncogene, vol. 19, pp. 4947-4953 (2000).

Lubensky, I. et al., "Hereditary and Sporadic Papillary Renal Carcinomas with c-*met* Mutations Share a Distinct Morphological Phenotype", American J. of Pathology, vol. 155(2), pp. 517-526 (1999).

Masuya, D. et al., "The tumor-stromal interaction between intratumoral c-Met and stromal hepatocyte growth factor associated with tumour growth and prognosis in non-small-cell lung cancer patients", British J. of Cancer, vol. 90, pp. 1555-1562 (2004).

Matsumoto, K. et al., "Hepatocyte Growth Factor: Molecular Structure, Roles in Liver Regeneration, and Other Biological Functions", Critical Reviews in Oncogenesis, vol. 3(1,2), pp. 27-54 (1992).

Montesano, R, et al., "Identification of a Fibroblast-Derived Epithelial Morphogen as Hepatocyte Growth Factor", Cell, vol. 67, pp. 901-908 (1991).

Park, M. et al., "Sequence of *MET* protooncogene cDNA has features characteristic of the tyrosine kinase family of growth-factor receptors", PNAS, vol. 84, pp. 6379-6383 (1987).

Rong, S. et al., "Met Expression and Sarcoma Tumorigenicity", Cancer Research, vol. 53, pp. 5355-5360 (1993).

Rong, S. et al., "Met Proto-oncogene Product Is Overexpressed in Tumors of p53-deficient Mice and Tumors of Li-Fraumeni Patients", Cancer Research, vol. 55, pp. 1963-1970 (1995).

Sachs, M. et al., "Essential Role of Gab1 for Signaling by the c-Met Receptor In Vivo", The J. of Cell Biology, vol. 150, pp. 1375-1384 (2000).

Scarpino, S. et al., "Hepatocyte Growth Factor (HGF) Stimulates Tumour Invasiveness in Papillary Carcinoma of the Thyroid", J. of Pathology, vol. 189, pp. 570-575 (1999).

Schaeper, U. et al., "Coupling of Gab1 to c-Met, Grb2, and Shp2 Mediates Biological Responses", The J. of Cell Biology, vol. 149, pp. 1419-1432 (2000).

Soman, N. et al., "The *TPR-MET* oncogenic rearrangement is present and expressed in human gastric carcinoma and precursor lesions", PNAS, vol. 88, pp. 4892-4896 (1991).

Sonnenberg, E. et al., "Scatter Factor/Hepatocyte Growth Factor and Its Receptor, the c-met Tyrosine Kinase, Can Mediate a Signal Exchange between Mesenchyme and Epithelia during Mouse Development", The J. of Cell Biology, vol. 123, pp. 223-235 (1993).

Stabile, L. et al., "Inhibition of human non-small cell lung tumors by a c-Met antisense/U6 expression plasmid strategy", Gene Therapy, vol. 11, pp. 325-335 (2004).

Stella, M. et al., "HGF: a multifunctional growth factor controlling cell scattering", The International J. of Biochemistry & Cell Biology, vol. 31, pp. 1357-1362 (1999).

Stoker, M. et al., "Scatter factor is a fibroblast-derived modulator of epithelial cell mobility", Nature, vol. 327, pp. 239-242 (1987).

Stuart, K. et al., "Hepatocyte growth factor/scatter factor-induced intracellular signaling", International J. of Experimental Pathology, vol. 81, pp. 17-30 (2000).

Takayama, H. et al., "Diverse tumorigenesis associated with aberrant development in mice overexpressing hepatocyte growth factor/scatter factor", PNAS, vol. 94, pp. 701-706 (1997).

Tanimura, S. et al., "Activation of the 41/43 kDa mitogen-activated protein kinase signaling pathway is required for hepatocyte growth factor-induced cell scattering", Oncogene, vol. 17, pp. 57-65 (1998).

Kubo et al., *Synthesis and Structure-Activity Relationship for New Series of 4-Phenoxyquinoline Derivatives as Specific Inhibitors of Platelet-Derived growth Factor Receptor Tyrosine Kinase*, Bio. Med. Chem., vol. 11, Aug. 2003, pp. 5117-5133.

Tsou et al., *Optimization of 6,7-Disubstituted-4-(arylamino)quinoline-3-carbonitriles as Orally Active, Irreverible Inhibitors of HEGFR-2 Kinase Activity*, J. Med. Chem., vol. 48, Jan. 27, 2005, pp. 1107-1131.

MET KINASE INHIBITORS

RELATED APPLICATION

This application claims priority benefit under Title 35 §119 (e) of U.S. provisional Application No. 60/716,864, filed Sep. 14, 2005, the contents of which are herein incorporated by reference.

FIELD OF THE INVENTION

This invention relates to compounds that inhibit the protein tyrosine kinase activity of growth factor receptors such as c-Met, thereby making them useful as anti-cancer agents. The pharmaceutical compositions that comprise these compounds are also useful in the treatment of diseases, other than cancer, which are associated with signal transduction pathways operating through growth factor and anti-angiogenesis receptors such as c-Met.

BACKGROUND OF THE INVENTION

Hepatocyte growth factor (HGF), also known as scatter factor (SF), because of its ability to disrupt colony formation in vitro, is a mesenchymally derived cytokine known to induce multiple pleiotropic responses in normal and neoplastic cells (Sonnenberg et al., *J. Cell Biol.* 123:223-235, 1993; Matsumato et al., *Crit. Rev. Oncog.* 3:27-54, 1992; and Stoker et al., *Nature* 327:239-242, 1987). These responses are known to include proliferation in both epithelial and endothelial cells, dissociation of epithelial colonies into individual cells, stimulation of motility (motogenesis) of epithelial cells, cell survival, induction of cellular morphogenesis (Montesano et al., *Cell* 67:901-908, 1991), and promotion of invasion (Stella et al., *Int. J. Biochem. Cell Biol.* 12:1357-62, 1999 and Stuart et al., *Int. J. Exp. Path.* 81:17-30, 2000), all critical processes underlying metastasis. HGF has also been reported to promote angiogenesis (Bussolino et al., *J. Cell Biol.* 119:629-641, 1992). In addition, HGF plays a critical role in tissue regeneration, wound healing, and normal embryonic processes, all of which are dependent on both cell motility and proliferation.

HGF initiates these physiological processes through high affinity binding to its cognate receptor, the Met protein tyrosine kinase receptor, an identified protooncogene (Park et al., *Proc. Natl. Acad. Sci. USA* 84:6379-83, 1987 and Bottaro et al., *Science* 251:802-4, 1991). The mature form of Met consists of a highly glycosylated external α-subunit as well as a β-subunit with a large extracellular domain, a transmembrane segment and a cytoplasmic tyrosine kinase domain. Ligand engagement induces Met dimerization that results in an autophosphorylated activated receptor. Activation of Met promotes signal transduction cascades as defined by transphosphorylation of key cytoplasmic tyrosine residues responsible for recruiting multiple effector proteins (Furge et al., *Oncogene* 19:5582-9, 2000). These include the p85 subunit of the PI3-kinase, phospholipase Cγ (Gaul et al., *Oncogene* 19:1509-18, 2000), Grb2 and Shc adaptor proteins, the protein phosphatase SHP2 and Gab1. The latter adapter has emerged as the major downstream docking molecule that becomes tyrosine phosphorylated in response to ligand occupancy (Schaeper et al., *J. Cell Biol.* 149:1419-32, 2000; Bardelli, et al., *Oncogene* 18:1139-46, 1999 and Sachs et al., *J. Cell Biol.* 150:1375-84, 2000). Activation of other signaling molecules has been reported in HGF stimulated cells, most notably Ras, MAP kinases, STATs, ERK-1, -2 and FAK (Tanimura et al., *Oncogene* 17:57-65, 1998; Lai et al., *J. Biol. Chem.* 275:7474-80 2000 and Furge et al., *Oncogene* 19:5582-9, 2000). The role of many of these signaling molecules has been well established in cell proliferation.

Met, also referred to as hepatocyte growth factor receptor (HGFR), is expressed predominantly in epithelial cells but has also been identified in endothelial cells, myoblasts, hematopoietic cells and motor neurons. Overexpression of HGF and activation of Met has been associated with the onset and progression in a number of different tumor types as well as in the promotion of metastatic disease. Initial evidence linking Met to cancer has been supported by the identification of kinase domain missense mutations, which predisposes individuals to papillary renal carcinomas (PRC) and hepatocellular carcinomas (HCC) (Lubensky et al., *Amer. J. Pathology*, 155:517-26, 1999). Mutated forms of Met have also been identified in ovarian cancer, childhood HCC, gastric carcinoma, head and neck squamous cell carcinoma, non-small cell lung carcinoma, colorectal metastasis (Christensen et al., *Cancer Res.*, 63:7345-55, 2003; Lee et al., *Oncogene*, 19:4947-53, 2000 and Direnzo et al., *Clin. Cancer Res.*, 1:147-54, 1995). In addition, further evidence supporting the role of the Met in cancer is based on the overexpression of HGF and Met receptor in various tumors including thyroid, ovarian and pancreatic carcinomas. It has also been demonstrated to be amplified in liver metastases of colorectal carcinomas (Rong et al. *Cancer Res.* 55:1963-1970, 1995; Rong et al., *Cancer Res.* 53:5355-5360, 1993; Kenworthy et al., *Br. J. Cancer* 66:243-247, 1992 and Scarpino et al. *J. Pathology* 189:570-575, 1999). TPR-Met (an activated form similar to BCR/Abl in CML) has been described and identified in human gastric carcinoma (PNAS 88:4892-6, 1991). In patients with invasive breast carcinoma and in a recent study in non small cell lung cancer patients, expression of either the receptor or ligand is a predictor of decreased survival, further linking Met to tumor progression (Camp et al., *Cancer* 86:2259-65 1999 and Masuya et al., *Br. J. Cancer*, 90:1555-62, 2004). In general, most human tumors and tumor cell lines of mesenchymal origin inappropriately express HGFR and/or HGF.

Numerous experimental data support the role of HGF and Met in tumor invasion, growth, survival and progression ultimately leading to metastases. Preclinically, transgenic expression of HGF results in a metastatic phenotype (Takayama et al., *PNAS*, 94:701-6, 1997) and an amplified/overexpressed Met spontaneously transforms NIH-3T3 cells (Cooper et al., *EMBO J.*, 5:2623-8, 1986).

Biological agents, such as ribozymes, antibodies and antisense RNA targeting either HGF or Met have been shown to inhibit tumorogenesis (Stabile et al., *Gene Therapy*, 11:325-35, 2004, Jiang et al., *Clin. Cancer Res*, 9:4274-81, 2003 and Genentech U.S. Pat. No. 6,214,344, 2001). Thus, selective, small molecule kinase modulators targeting Met are expected to have therapeutic potential for the treatment of cancers in which Met receptor activation plays a critical role in the development and progression of primary tumors and secondary metastases. HGF is also known to regulate angiogenesis, a process critical in tumor growth and dissemination. Therefore, there is a potential for this class of modulators to impact angiogenesis-dependent diseases as well that may include among others, diabetic retinopathy, macular degeneration, obesity and inflammatory disease such as rheumatoid arthritis.

SUMMARY

The present invention is directed to compounds having one of the following formula I, II, or IIII:

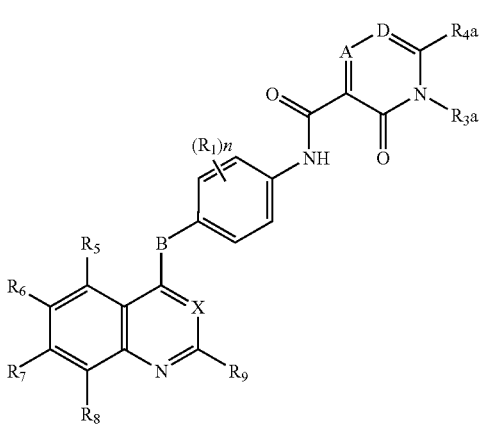

I

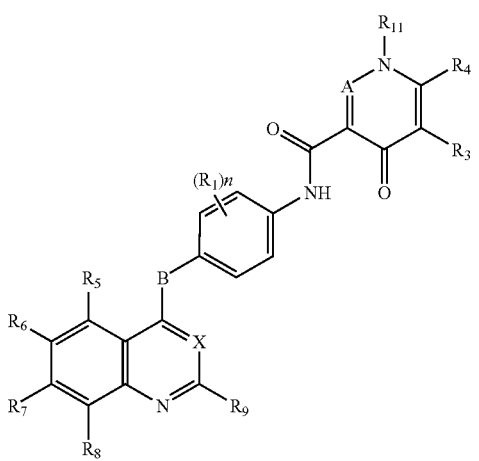

II

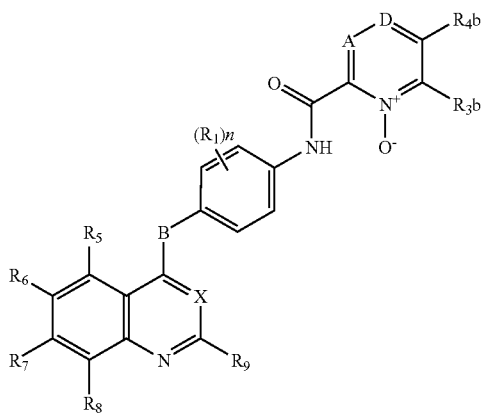

III wherein:

X is —CR$^{12}$ or N;

B is O, S, —SO, —SO$_2$, —NR$^a$, or —C(R$^b$)(R$^c$)—;

A is —CR$^d$ or N;

D is —CR$^e$ or N;

l is 0 to 6;

each R$^1$ is independently H, halogen, cyano, NO$_2$, OR$^{13}$, NR$^{14}$R$^{15}$, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, aralkyl, substituted arylalkyl, heterocycloalkyl, or substituted heterocycloalkyl;

R$^3$, R$^{3b}$, R$^4$, R$^{4a}$, R$^{4b}$, R$^9$, R$^d$ and R$^e$ are independently H; alkyl, substituted alkyl, alkenyl, substituted alkenyl, alkynyl, substituted alkynyl, —CN, hydroxyl, halo, amino, alkylthio, alkoxy, aryl, heterocycloalkyl, aralkyl, alkylaryl, aminoalkylamino, or alkylaminoalkoxy;

R$^{3a}$ is H, alkyl, substituted alkyl, alkenyl, substituted alkenyl, alkynyl, substituted alkynyl, —CN, hydroxyl, amino, alkylthio, alkoxy, aryl, heterocycloalkyl, aralkyl, alkylaryl, aminoalkylamino, or alkylaminoalkoxy;

R$^5$, R$^6$, R$^7$, R$^8$ and R$^{12}$ are independently H, halogen, NO$_2$, cyano, —OR$^{13}$, —NR$^{14}$R$^{15}$, —CO$_2$R$^{16}$, —C(O)NR$^{14}$R$^{15}$, —SO$_2$R$^{16}$, —SO$_2$NR$^{14}$R$^{15}$, —NR$^{14}$SO$_2$R$^{15}$, —NR$^{14}$C(O)R$^{15}$, —NR$^{14}$CO$_2$R$^{15}$, —CO(CH$_2$)$_l$R$^{15}$, —CONH(CH$_2$)$_l$R$^{16}$, alkylaminoalkyl, alkylaminoalkynyl, C$_1$ to C$_6$ alkyl, substituted C$_1$ to C$_6$ alkyl, cycloalkyl, substituted cycloalkyl, alkenyl, substituted alkenyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl;

R$^{11}$ is H, C$_1$ to C$_6$ alkyl, substituted C$_1$ to C$_6$ alkyl, C$_3$ to C$_7$ cycloalkyl, substituted C$_3$ to C$_7$ cycloalkyl, —OR$^{13}$, aryl, substituted aryl, heteroaryl, substituted C$_5$ to C$_{14}$ heteroaryl, arylalkyl, substituted arylalkyl, heteroarylalkyl, substituted heteroarylalkyl, heterocycloalkyl, substituted heterocycloalkyl, heterocycloalkylalkyl or substituted heterocycloalkylalkyl;

R$^a$, R$^{13}$, R$^{14}$, R$^{15}$, and R$^{16}$ are independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl;

R$^b$ and R$^c$ are independently H, alkyl, substituted alkyl, cycloalkyl, substituted cycloalkyl, aryl, substituted aryl, heteroaryl, substituted heteroaryl, heterocycloalkyl, substituted heterocycloalkyl or taken together to form a carbocyclic or heterocyclic ring of 3 to 8 atoms.

The present invention is also directed to methods of treating cancer comprising administering to a patient in need of such treatment a compound having Formula I, II, or III.

The present invention is also directed to pharmaceutical compositions comprising at least one compound having formula I, II, or III, in a pharmaceutically acceptable carrier.

DETAILED DESCRIPTION OF THE INVENTION

The present invention provides for compounds having Formula I, II or III, as defined above, pharmaceutical compositions employing such compounds, methods of making and methods of using such compounds.

Listed below are definitions of various terms used to describe the compounds of the instant invention. These definitions apply to the terms as they are used throughout the specification (unless they are otherwise limited in specific instances) either individually or as part of a larger group.

The term "alkyl" herein alone or as part of another group refers to a monovalent alkane (hydrocarbon) derived radical containing from 1 to 12 carbon atoms unless otherwise defined. Preferred alkyl groups have from 1 to 6 carbon atoms. An alkyl group is an optionally substituted straight, branched or cyclic saturated hydrocarbon group. Alkyl groups may be substituted at any available point of attachment. An alkyl group substituted with another alkyl group is also referred to as a "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Alkyl groups may be substituted with substituents selected from the following: alkyl, aryl, aryloxy, halo (such as F, Cl, Br, I), haloalkyl (such as CCl₃ or CF₃), alkoxy, alkylthio, hydroxy, carboxy (—COOH), alkyloxycarbonyl (—C(O)nR), alkylcarbonyloxy (—OCOR), amino (—NR'R"), carbamoyl (—NHCOOR— or —OCONHR—), urea (—NHCONHR—) or thiol (—SH).

The term "alkenyl" herein alone or as part of another group refers to a hydrocarbon radical straight, branched or cyclic, containing from 2 to 12 carbon atoms and at least one carbon to carbon double bond. Alkenyl groups may also be substituted at any available point of attachment. Exemplary substituents for alkenyl groups include those listed above for alkyl groups, and especially include $C_3$ to $C_7$ cycloalkyl groups such as cyclopropyl, cyclopentyl and cyclohexyl, which may be further substituted with, for example, amino, oxo, hydroxyl, etc.

The term "alkynyl" herein alone or as part of another group refers to a hydrocarbon radical straight, branched or cyclic containing from 2 to 12 carbon atoms and at least one carbon to carbon triple bond. Alkynyl groups may also be substituted at any available point of attachment. Exemplary substituents for alkynyl groups include those listed above for alkyl groups such as amino, alkylamino, etc.

The numbers in the subscript after the symbol "C" define the number of carbon atoms a particular group can contain. For example "$C_1$ to $C_6$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_1$ to $C_6$ alkyl" can also refer to $C_1$ to $C_6$ alkylene which bridges two groups; examples include propane-1,3-diyl, butane-1,4-diyl, 2-methyl-butane-1,4-diyl, etc. "$C_2$ to $C_6$ alkyenyl means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_2$ to $C_6$ alkenyl" can also refer to $C_2$ to $C_6$ alkenediyl which bridges two groups; examples include ethylene-1,2-diyl (vinylene), 2-methyl-2-butene-1,4-diyl, 2-hexene-1,6-diyl, etc. "$C_2$ to $C_6$ alkynyl" means a straight or branched carbon chain having at least one carbon-carbon triple bond, and from two to six carbon atoms; examples include ethynyl, propynyl, butynyl, and hexynyl.

The term "acyl" herein alone or as part of another group refers to an alkyl group bonded through a carbonyl group or —C(O)R.

The term "alkoxy" herein alone or as part of another group denotes an alkyl group, preferably having from 1 to 6 carbon atoms, bonded through an oxygen atom, such as —OR, wherein R is the alkyl group.

The term "alkyloxycarbonyl" herein alone or as part of another group refers to —C(O)OR, wherein R is an alkyl group.

The term "arylalkyl" or "aralkyl" herein alone or as part of another group denotes an aromatic ring bonded through an alkyl group (such as benzyl) as described above.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Preferred aryl groups contain from 6 to 14 carbon atoms in the rings. Aryl groups may optionally be substituted with one or more groups including, but not limited to halogen, such as Br, F, or Cl, alkyl, such as methyl, ethyl, propyl, alkoxy, such as methoxy or ethoxy, hydroxy, carboxy, carbamoyl, alkyloxycarbonyl, nitro, alkenyloxy, trifluoromethyl, amino, cycloalkyl, aryl, heteroaryl, cyano, alkyl $S(O)_m$ (m=0, 1, 2), or thiol.

The term "amino" herein alone or as part of another group refers to —NH₂. An "amino" may optionally be substituted with one or two substituents (NR'R"), wherein R' and R" may be the same or different, such as alkyl, aryl, arylalkyl, alkenyl, alkynyl, heteroaryl, heteroarylalkyl, heterocycloalkyl, alkyl, alkylalkyl, cycloalkyl, cycloalkylalkyl, haloalkyl, hydroxyalkyl, alkoxyalkyl, thioalkyl, carbonyl or carboxyl. These substituents may be further substituted with a carboxylic acid, or any of the alkyl or aryl substituents set out herein. In some embodiments, the amino groups are substituted with carboxyl or carbonyl to form N-acyl or N-carbamoyl derivatives.

The term "cycloalkyl" herein alone or as part of another group refers to fully saturated and partially unsaturated hydrocarbon rings of 3 to 9, preferably 3 to 7 carbon atoms. Further, a cycloalkyl may be substituted. A substituted cycloalkyl refers to such rings having one, two, or three substituents, selected from the group consisting of halo, alkyl, substituted alkyl, wherein the substituents are defined as above for alkyl substituents, alkenyl, alkynyl, nitro, cyano, oxo (=O), hydroxy, alkoxy, thioalkyl, —CO₂H, —C(=O)H, CO₂-alkyl, —C(=O)alkyl, keto, =N—OH, =N—O-alkyl, aryl, heteroaryl, heterocycloalkyl, a five or six membered ketal (i.e. 1,3-dioxolane or 1,3-dioxane), —NR'R", —C(=O)NR'R", —CO₂NR'R", —C(=O)NR'R", —NR'CO₂R", —NR'C(=O)R", —SO₂NR'R", and —NR'SO₂R", wherein each of R' and R" are independently selected from hydrogen, alkyl, substituted alkyl, and cycloalkyl, or R' and R" together form a heterocycloalkyl or heteroaryl ring.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, aryl, nitro, cyano, hydroxy, alkoxy, thioalkyl, —CO₂H, —C(=O)H, —CO₂-alkyl, —C(=O) alkyl, phenyl, benzyl, phenylethyl, phenyloxy, phenylthio, cycloalkyl, substituted cycloalkyl, heterocycloalkyl, heteroaryl, —NR'R", —C(=O)NR'R", —CO₂NR'R", —C(=O)NR'R", —NR'CO₂R", —NR'C(=O)R", —SO₂NR'R", and —NR'SO₂R", wherein each of R' and R" is independently selected from hydrogen, alkyl, substituted alkyl, and cycloalkyl, or R' and R" together form a heterocycloalkyl or heteroaryl ring.

Exemplary monocyclic heteroaryl groups include pyrrolyl, pyrazolyl, pyrazolinyl, imidazolyl, oxazolyl, diazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl and the like.

Exemplary bicyclic heteroaryl groups include indolyl, benzothiazolyl, benzodioxolyl, benzoxaxolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzidolyl, phenanthrollinyl, acridinyl, phenanthridinyl, xanthenyl and the like.

The term "heterocycloalkyl" herein alone or as part of another group refers to a cycloalkyl group (nonaromatic) in which one of the carbon atoms in the ring is replaced by a heteroatom selected from O, S or N, and in which up to three additional carbon atoms may be replaced by said heteroatoms. The term "heterocycloalkyl" herein alone or as part of another group refers to a stable, saturated, or partially unsaturated monocyclic ring system containing 5 to 7 ring members of carbon atoms and other atoms selected from nitrogen, sulfur and/or oxygen. A heterocyclic ring may be a 5, 6 or 7-membered monocyclic ring and contain one, two, or three heteroatoms selected from nitrogen, oxygen and/or sulfur. The heterocyclic ring may be optionally substituted which means that the heterocyclic ring may be substituted at one or more substitutable ring positions by one or more groups independently selected from alkyl (preferably lower alkyl), heterocycloalkyl, heteroaryl, alkoxy (preferably lower alkoxy), nitro, monoalkylamino (preferably a lower alkylamino), dialkylamino (preferably a di[lower]alkylamino), cyano, halo, haloalkyl (preferably trifluoromethyl), alkanoyl, aminocarbonyl, monoalkylaminocarbonyl, dialkylaminocarbonyl, alkyl amido (preferably lower alkyl amido), alkoxyalkyl (preferably a lower alkoxy[lower]alkyl), alkoxycarbonyl (preferably a lower alkoxycarbonyl), alkylcarbonyloxy (preferably a lower alkylcarbonyloxy) and aryl (preferably phenyl), said aryl being optionally substituted by halo, lower alkyl and lower alkoxy groups. Examples of such heterocycloalkyl groups include piperazine, piperidine, morpholine, homomorpholine, thiomorpholine, pyrrolidine, and azetidine.

The term "heteroatom" means O, S or N, selected on an independent basis. It should be noted that any heteroatom with unsatisfied valences is assumed to have the hydrogen atom to satisfy the valences.

The term "halogen" or "halo" refers to chlorine, bromine, fluorine or iodine selected on an independent basis.

The phrase "gene amplification," as used herein means the selective synthesis of a DNA fragment that results in multiple copies of the Met gene or fragment of the chromosome in which Met is encoded.

The phrase "activated Met mutation" as used herein means a selective change in the DNA sequence of Met resulting in a Met protein that is constitutively (i.e., permanently) phosphorylated.

The phrase "HGF stimulation," as used herein means the ability of a HGF to bind its cognate receptor (Met) in such a way as to activate the receptor that results in a phenotypic response. In the case of Met, this can be cellular proliferation, motility, differentiation and/or survival.

The term "anticancer" agent includes any known agent that is useful for the treatment of cancer including the following: 17α-ethinylestradiol, diethylstilbestrol, testosterone, prednisone, fluoxymesterone, dromostanolone propionate, testolactone, megestrolacetate, methylprednisolone, methyl-testosterone, prednisolone, triamcinolone, chlorotrianisene, hydroxyprogesterone, aminoglutethimide, estramustine, medroxyprogesteroneacetate, leuprolide, flutamide, toremifene, Zoladex; matrix metalloproteinase inhibitors; VEGF inhibitors, such as anti-VEGF antibodies (Avastin,) and small molecules such as ZD6474, AZD-2171, and SU6668; Vatalanib, BAY-43-9006, SU11248, CP-547632, and CEP-7055; Her 1 and Her 2 inhibitors including anti-Her2 antibodies (Herceptin); EGFR inhibitors including gefitinib, erlotinib, ABX-EGF, EMD72000, 11F8, and cetuximab; Eg5 inhibitors, such as SB-715992, SB-743921, and MKI-833; pan Her inhibitors, such as canertinib, EKB-569, CI-1033, AEE-788, XL-647, mAb 2C4, and GW-572016; Src inhibitors, BMS-354825, AZD-0530 and SKI-606, and AP-23464; Casodex®, Bcr-Abl inhibitors (GLEEVAC), (bicalutamide, Astra Zeneca), Tamoxifen; MEK-1 kinase inhibitors, MAPK kinase inhibitors, PI3 kinase inhibitors; Met inhibitors, aurora kinase inhibitors, PDGF inhibitors, such as imatinib; anti-angiogenic and antivascular agents which, by interrupting blood flow to solid tumors, render cancer cells quiescent by depriving them of nutrition; castration, which renders androgen dependent carcinomas non-proliferative; IGF1R inhibitors such as those disclosed in U.S. Ser. No. 2004/44203A1, inhibitors of non-receptor and receptor tyrosine kinases; inhibitors of integrin signaling; tubulin acting agents such as vinblastine, vincristine, vinorelbine, vinflunine, paclitaxel, docetaxel, 7-O-methylthiomethylpaclitaxel, 4-desacetyl-4-methylcarbonatepaclitaxel, 3'-tert-butyl-3'-N-tert-butyloxycarbonyl-4-deacetyl-3'-dephenyl-3'-N-debenzoyl-4-O-methoxycarbonyl-paclitaxel, C-4 methyl carbonate paclitaxel, epothilone A, epothilone B, epothilone C, epothilone D, desoxyepothilone A, desoxyepothilone B, ixabepilone, [1S-[1R*,3R*(E),7R*,10S*,11R*,12R*, 16S*]]-3-[2-[2-(aminomethyl)-4-thiazolyl]-1-methylethenyl]-7,11-dihydroxy-8,8,10,12,16-pentamethyl-4-17-dioxabicyclo[14.1.0]-heptadecane-5,9-dione, and derivatives thereof; CDK inhibitors, antiproliferative cell cycle inhibitors, epidophyllotoxin, etoposide, VM-26; antineoplastic enzymes, e.g., topoisomerase I inhibitors, camptothecin, topotecan, SN-38; procarbazine; mitoxantrone; platinum coordination complexes such as cisplatin, carboplatin and oxaliplatin; biological response modifiers; growth inhibitors; antihormonal therapeutic agents; leucovorin; tegafur; antimetabolites such as purine antagonists (e.g. 6-thioguanine and 6-mercaptopurine; glutamine antagonists, e.g. DON (AT-125; d-oxo-norleucine); ribonucleotide reductase inhibitors; mTOR inhibitors; and haematopoietic growth factors.

Additional cytotoxic agents include, cyclophosphamide, doxorubicin, daunorubicin, mitoxanthrone, melphalan, hexamethyl melamine, thiotepa, cytarabin, idatrexate, trimetrexate, dacarbazine, L-asparaginase, bicalutamide, leuprolide, pyridobenzoindole derivatives, interferons, and interleukins.

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

As used herein, the term "patient" encompasses all mammalian species, including humans, cowes, horses, dogs, and cats.

The phrase "pharmaceutically effective" is intended to qualify the amount of each agent, which will achieve the goal of improvement in disorder severity and the frequency of incidence over treatment of each agent by itself, while avoiding adverse side-effects typically associated with alternative therapies. For example, effective anticancer agents prolong the survivability of the patient, inhibit the rapidly proliferating cell growth associated with the neoplasm, or effect a regression of the neoplasm.

The phrase "pharmaceutically acceptable salt(s)", or "salt" as used herein, unless otherwise indicated, includes salts of acidic or basic groups which may be present in the compounds of the present invention. The compounds of formulae I, II and III that are basic in nature are capable of forming a wide variety of salts with various inorganic and organic acids. Accordingly, compounds having Formula I, II and III include both the free base and salt forms. The acids that may be used to prepare pharmaceutically acceptable acid addition salts of such basic compounds of formulae I, II and III are those that form non-toxic acid addition salts, i.e., salts containing pharmacologically acceptable anions, such as the hydrochloride, hydrobromide, hydroiodide, nitrate, sulfate, bisulfate, phosphate, acid phosphate, isonicotinate, acetate, lactate, salicylate, citrate, acid citrate, tartrate, pantothenate, bitartrate, ascorbate, succinate, maleate, gentisinate, fumarate, gluconate, glucaronate, mesylate, saccharate, formate, benzoate, glutamate, methanesulfonate, ethanesulfonate, benzenesulfonate, p-toluenesulfonate and pamoate [i.e., 1,1'-methylene-bis-(2-hydroxy-3-naphthoate)]salts.

According to one embodiment of the present invention, methods are provided for treating a proliferative disease via modulation of Met kinase by administering to a patient in need of such treatment a therapeutically effective amount of a compound of formula I, II, or II as defined above, in combination (simultaneously or sequentially) with at least one other anti-cancer agent. In a preferred embodiment, the proliferative disease is cancer.

The invention further provides pharmaceutical compositions comprising a pharmaceutically effective amount of a compound having formula I, II or III together with a pharmaceutically acceptable carrier.

The compounds of the present invention have either Formula I, II or III:

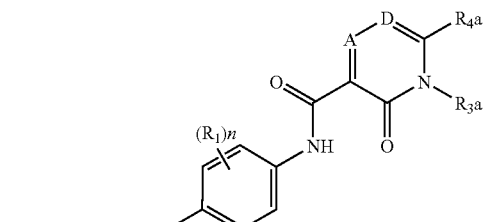

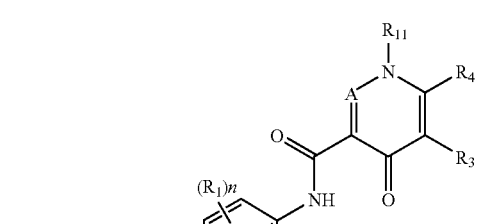

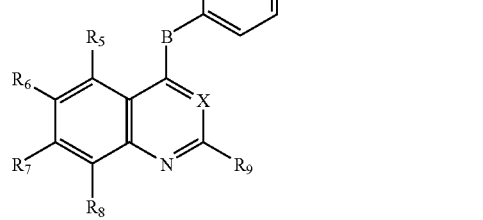

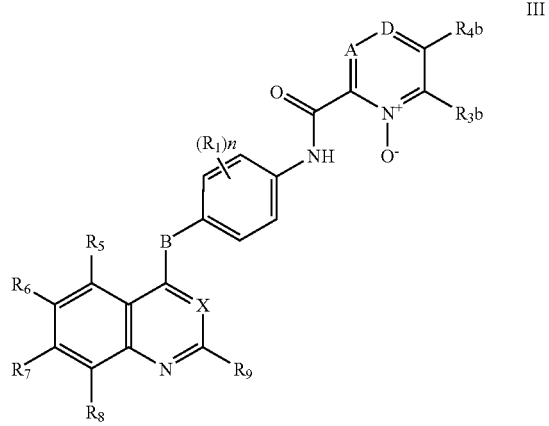

wherein:
X is $—CR^{12}$ or N;
B is O, S, —SO, $—SO_2$, $—NR^a$, or $—C(R^b)(R^c)—$;
A is $—CR^d$ or N;
D is $—CR^e$ or N;
each $R^1$ is independently H, halogen, cyano, $NO_2$, $OR^{13}$, $NR^{14}R^{15}$, alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, aryalkyl, substituted arylalkyl, heterocycloalkyl, or substituted heterocycloalkyl;
$R^3$, $R^{3b}$, $R^4$, $R^{4a}$, $R^{4b}$, $R^9$, $R^d$ and $R^e$ are each independently H, alkyl, substituted alkyl, alkenyl, substituted alkenyl, alkynyl, substituted alkynyl, —CN, hydroxyl, halo, amino, alkylthio, alkoxy, aryl, heterocycloalkyl, aralkyl, alkylaryl, aminoalkylamino, or alkylaminoalkoxy;
$R^{3a}$ is H, alkyl, substituted alkyl, alkenyl, substituted alkenyl, alkynyl, substituted alkynyl, —CN, hydroxyl, amino, alkylthio, alkoxy, aryl, heterocycloalkyl, aralkyl, alkylaryl, aminoalkylamino, or alkylaminoalkoxy;
$R^5$, $R^6$, $R^7$, $R^8$ and $R^{12}$ are each independently H, halogen, $NO_2$, cyano, $—OR^{13}$, $—NR^{14}R^{15}$, $—CO_2R^{16}$, $—C(O)NR^{14}R^{15}$, $—SO_2R^{16}$, $—SO_2NR^{14}R^{15}$, $—NR^{14}SO_2R^{15}$, $—NR^{14}C(O)R^{15}$, $—NR^{14}CO_2R^{15}$, $—CO(CH_2)_1R^{15}$, $—CONH(CH_2)_1R^{16}$, alkylaminoalkyl, alkylaminoalkynyl, $C_1$ to $C_6$ alkyl, substituted $C_1$ to $C_6$ alkyl, cycloalkyl, substituted cycloalkyl, alkenyl, substituted alkenyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl;
$R^{11}$ is H, $C_1$ to $C_6$ alkyl, substituted $C_1$ to $C_6$ alkyl, $C_3$ to $C_7$ cycloalkyl, substituted $C_3$ to $C_7$ cycloalkyl, $—OR^{13}$, aryl, substituted aryl, heteroaryl, substituted $C_5$ to $C_{14}$ heteroaryl, arylalkyl, substituted arylalkyl, heteroarylalkyl, substituted heteroarylalkyl, heterocycloalkyl, substituted heterocycloalkyl, heterocycloalkylalkyl or substituted heterocycloalkylalkyl;
$R^a$, $R^{13}$, $R^{14}$, $R^{15}$, and $R^{16}$ are each independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl;
$R^b$ and $R^c$ are each independently H, alkyl, substituted alkyl, cycloalkyl, substituted cycloalkyl, aryl, substituted aryl, heteroaryl, substituted heteroaryl, heterocycloalkyl, substituted heterocycloalkyl or taken together to form a carbocyclic or heterocyclic ring of 3 to 8 atoms.

According to one embodiment of the present invention, A is CH.

According to one embodiment of the present invention, D is CH or N.

According to one embodiment of the present invention, $R^{4a}$ or $R^d$ is hydroxyl, halo, $C_1$ to $C_4$alkyl, $C_3$ to $C_7$ cycloalkyl, CN, alkylthio, alkoxy, phenyl, amino, heterocycloalkyl, aminoalkylamino or alkylaminoalkoxy.

According to one embodiment of the present invention, $R^{3a}$ is phenyl.

According to one embodiment of the present invention, $R^3$ is benzyl.

According to one embodiment of the present invention, at least one of $R^6$ and $R^7$ is —OH, —OCH$_3$, or —OCH$_2$-piperidine.

According to one embodiment of the present invention, $R_1$ is F, $R^2$ is H, $R^{3a}$ is phenyl, $R^{4a}$ is H, and at least one of $R^6$ or $R^7$ is —OH, —OCH$_3$, or —OCH$_2$-piperidine.

According to one embodiment of the present invention, $R_1$ is F, $R^2$ is H, $R^3$ is benzyl, $R^4$ is H, and at least one of $R^6$ and $R^7$ is —OCH$_3$.

The compounds of Formulas I, II and III are useful in the treatment of a variety of cancers, including, but not limited to, the following:

a) carcinoma, including that of the bladder, breast, colon, kidney, liver, lung, including small cell lung cancer, esophagus, gall bladder, ovary, pancreas, stomach, cervix, thyroid, prostate, and skin, including squamous cell carcinoma;

b) hematopoietic tumors of lymphoid lineage, including leukemia, acute lymphocytic leukemia, acute lymphoblastic leukemia, B-cell lymphoma, T-cell lymphoma, Hodgkin's lymphoma, non-Hodgkins lymphoma, hairy cell lymphoma and Burkett's lymphoma;

c) hematopoietic tumors of myeloid lineage, including acute and chronic myelogenous leukemias, myelodysplastic syndrome and promyelocytic leukemia;

d) tumors of mesenchymal origin, including fibrosarcoma and rhabdomyosarcoma;

e) tumors of the central and peripheral nervous system, including astrocytoma, neuroblastoma, glioma and schwannomas; and f) other tumors, including melanoma, seminoma, teratocarcinoma, osteosarcoma, xenoderoma pigmentosum, keratoctanthoma, thyroid follicular cancer and Kaposi's sarcoma.

Preferably, the compounds of the present invention are useful in the treatment of a variety of cancers, most preferably, those cancers that are dependent upon Met activation. Met activation may be regulated by gene amplification, mutation(s) and/or HGF stimulation in which HGF is provided by either the tumor (autocrine) or host (paracrine) tissues. Thus, the present invention is also directed to methods of treating cancers such as the following bladder breast, colorectal, gastric, head and neck, kidney, liver, lung, ovarian, pancreas/gall bladder, prostate, thyroid, osteosarcoma, rhabdomyosarcoma, MFH/fibrosarcoma, glioblastomas/astrocytomas, melanoma, and mesothelioma.

Due to the key role protein kinases in the regulation of cellular proliferation in general, inhibitors could act as reversible cytostatic agents which may be useful in the treatment of any disease process which features abnormal cellular proliferation, e.g., benign prostatic hyperplasia, familial adenomatosis polyposis, neuro-fibromatosis, atherosclerosis, pulmonary fibrosis, arthritis, psoriasis, glomerulo-nephritis, restenosis following angioplasty or vascular surgery, hypertrophic scar formation, inflammatory bowel disease, transplantation rejection, endotoxic shock, and fungal infections.

Compounds of the present invention as modulators of apoptosis, will be useful in the treatment of cancer (including but not limited to those types mentioned herein above), viral infections (including but not limited to herpevirus, poxvirus, Epstein-Barr virus, Sindbis virus and adenovirus), prevention of AIDS development in HIV-infected individuals, autoimmune diseases (including but not limited to systemic lupus, erythematosus, autoimmune mediated glomerulonephritis, rheumatoid arthritis, psoriasis, inflammatory bowel disease, and autoimmune diabetes mellitus), neurodegenerative disorders (including but not limited to Alzheimer's disease, AIDS-related dementia, Parkinson's disease, amyotrophic lateral sclerosis, retinitis pigmentosa, spinal muscular atrophy and cerebellar degeneration), myelodysplastic syndromes, aplastic anemia, ischemic injury associated with myocardial infarctions, stroke and reperfusion injury, arrhythmia, atherosclerosis, toxin-induced or alcohol related liver diseases, hematological diseases (including but not limited to chronic anemia and aplastic anemia), degenerative diseases of the musculoskeletal system (including but not limited to osteoporosis and arthritis) aspirin-sensitive rhinosinusitis, cystic fibrosis, multiple sclerosis, kidney diseases and cancer pain.

Compounds of the invention may modulate the level of cellular RNA and DNA synthesis. These agents would therefore be useful in the treatment of viral infections (including but not limited to HIV, human papilloma virus, herpesvirus, poxvirus, Epstein-Barr virus, Sindbis virus and adenovirus).

Compounds of the invention may be useful in the chemoprevention of cancer. Chemoprevention is defined as inhibiting the development of invasive cancer by either blocking the initiating mutagenic event or by blocking the progression of pre-malignant cells that have already suffered an insult or inhibiting tumor relapse.

Compounds of the invention may also be useful in inhibiting tumor angiogenesis and metastasis.

The compounds of this invention may also be useful in combination (administered together or sequentially) with known anti-cancer agents or treatments, as herein described above.

The pharmaceutical compositions containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients or carriers which are suitable for the manufacture of tablets. These excipients or carriers may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinyl-pyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropylcellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinylpyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS™ model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of the invention may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compounds of the present invention are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of the invention may also be administered sequentially with known anticancer or cytotoxic agents when a combination formulation is inappropriate. The invention is not limited in the sequence of administration; compounds of the invention may be administered either prior to or after administration of the known anticancer or cytotoxic agent(s).

Compounds of the invention may generally be prepared according to the following Schemes 1 to 5. Tautomers and solvates (e.g., hydrates) of the compounds of the invention are also within the scope of the present invention. Methods of solvation are generally known in the art. Accordingly, the compounds of the instant invention may be in the free or hydrate form, and may be obtained by methods exemplified by the following schemes.

Dimethoxy substituted quinoline analogue was prepared generally as shown in Scheme 1. Substituted quinolone 2 was synthesized by reacting aminoacetophenone 1 with ethyl formate in the presence of base such as sodium methoxide as described generally in the literature (J. Med. Chem., 2005, 48, 1359-1366, herein incorporated by reference in its entirety). Coupling of the quinolone 2 with di-fluoronitrobenzene 3 in the presence of cesium carbonate afforded a mixture of O- and N-alkylation adducts. The desired O-alkylation compound 4 was reduced using zinc metal to obtain the amino compound 5. Substituted pyridone acid 9 can be obtained by reacting pyrone 6 (Aldrich) with 4-fluoroaniline followed by intramolecular cyclization of the initial Michael adduct and hydrolysis. Coupling of aniline 5 with pyridone acid 9 using EDCI and HOBt reagents provided quinoline analogue 10.

SCHEME 1

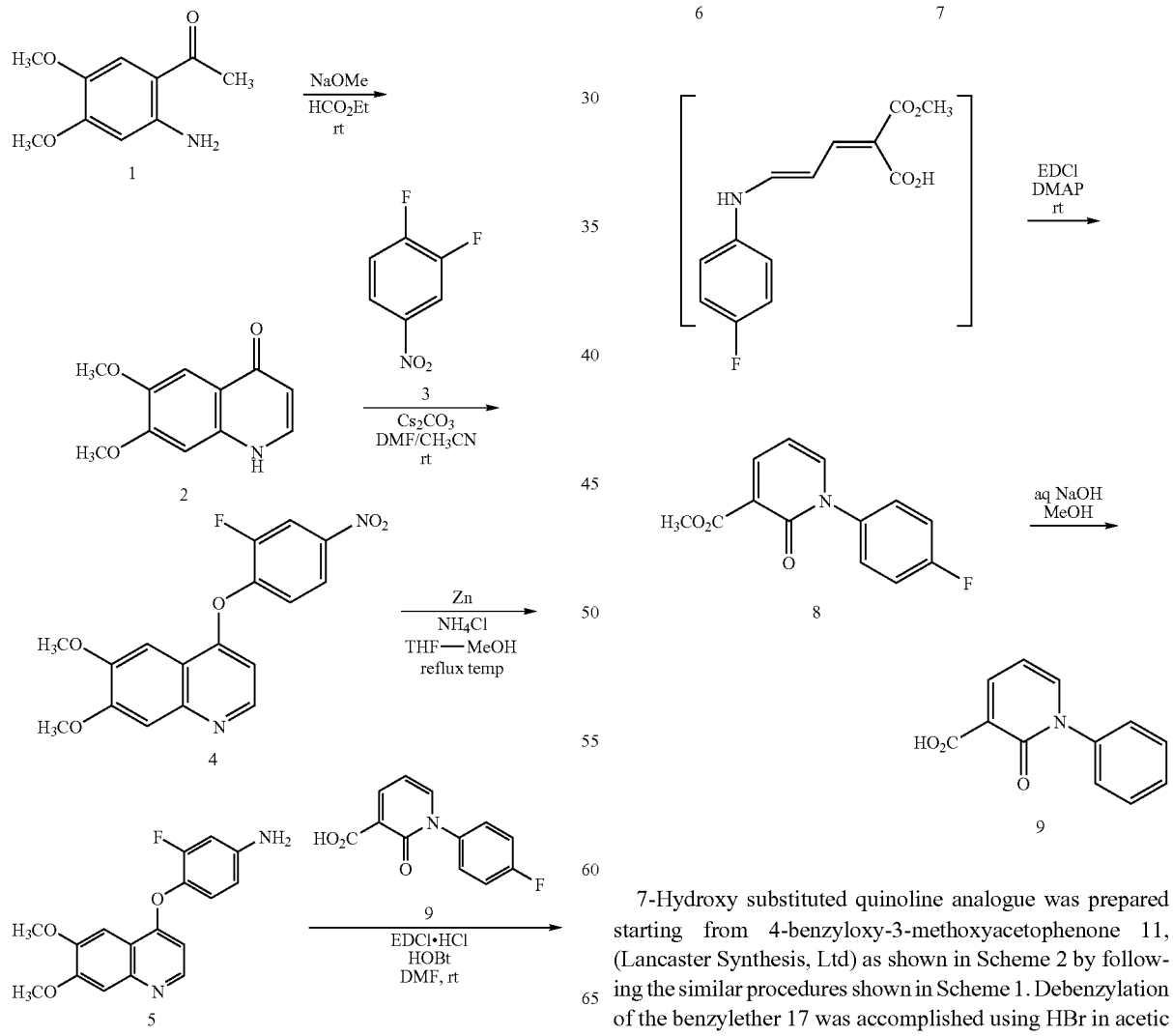

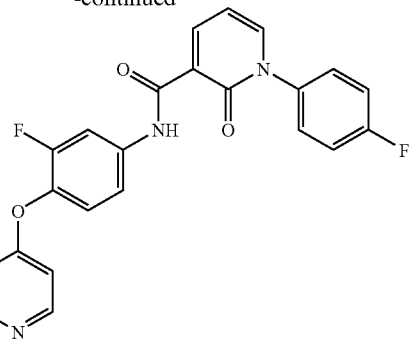

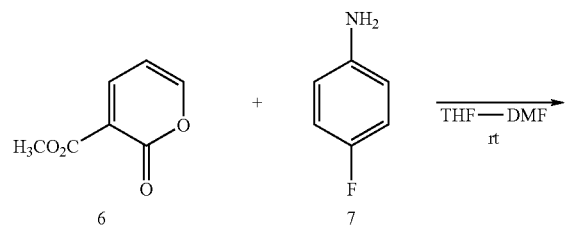

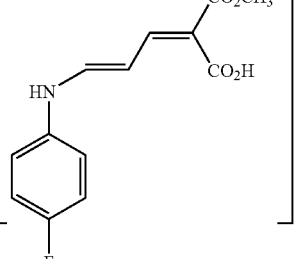

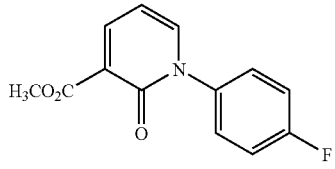

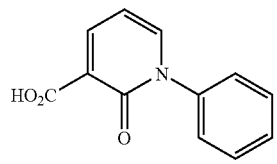

7-Hydroxy substituted quinoline analogue was prepared starting from 4-benzyloxy-3-methoxyacetophenone 11, (Lancaster Synthesis, Ltd) as shown in Scheme 2 by following the similar procedures shown in Scheme 1. Debenzylation of the benzylether 17 was accomplished using HBr in acetic acid to obtain 7-hydroxyquinoline analogue 18.

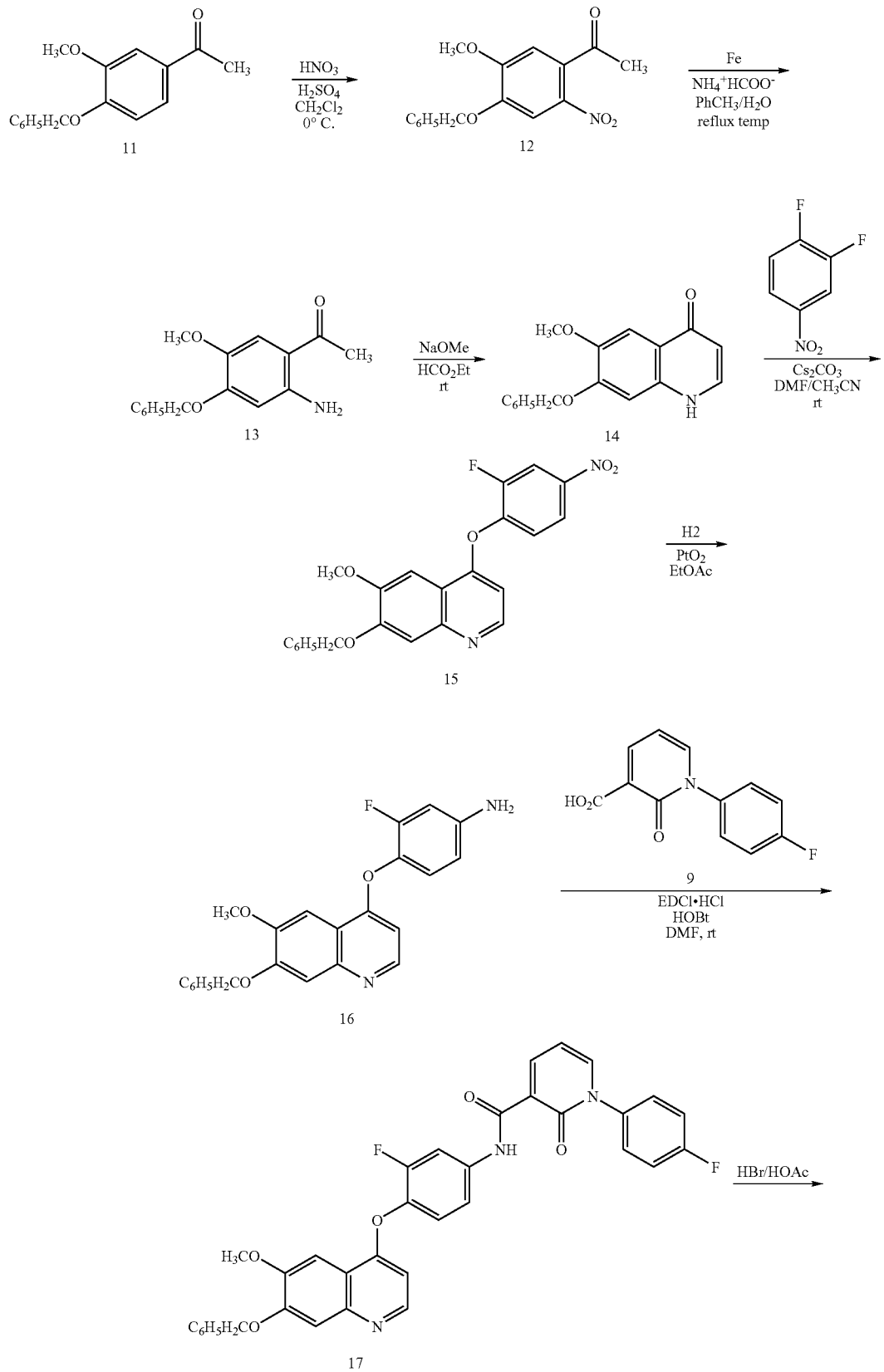

-continued

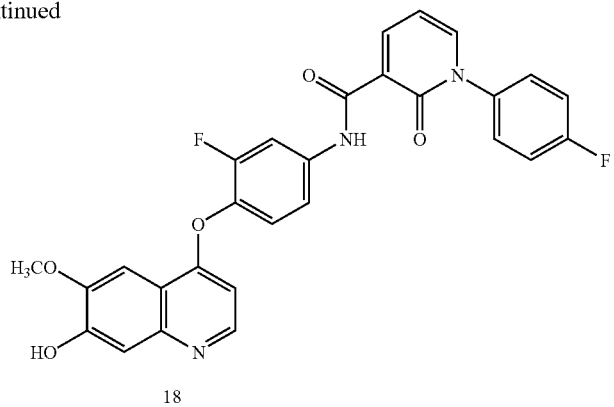
18

Quinoline analogue having the piperidyl moiety at C-7 side chain of the quinoline was prepared by introducing the piperidylmethyl to the C-7 hydroxyl of quinoline 19 (Scheme 3). 7-Hydroxy quinoline 19 was obtained by debenzylation of 15 with HBr/acetic acid. The nitro group of the compound 21 was reduced by catalytic hydrogenation with Pd(OH)$_2$, which was coupled with pyridone acid 9 to obtain quinoline 23. Deprotection of 23 using trifluoroacetic acid followed by methylation provide quinoline analogues 24 and 25, respectively.

SCHEME 3

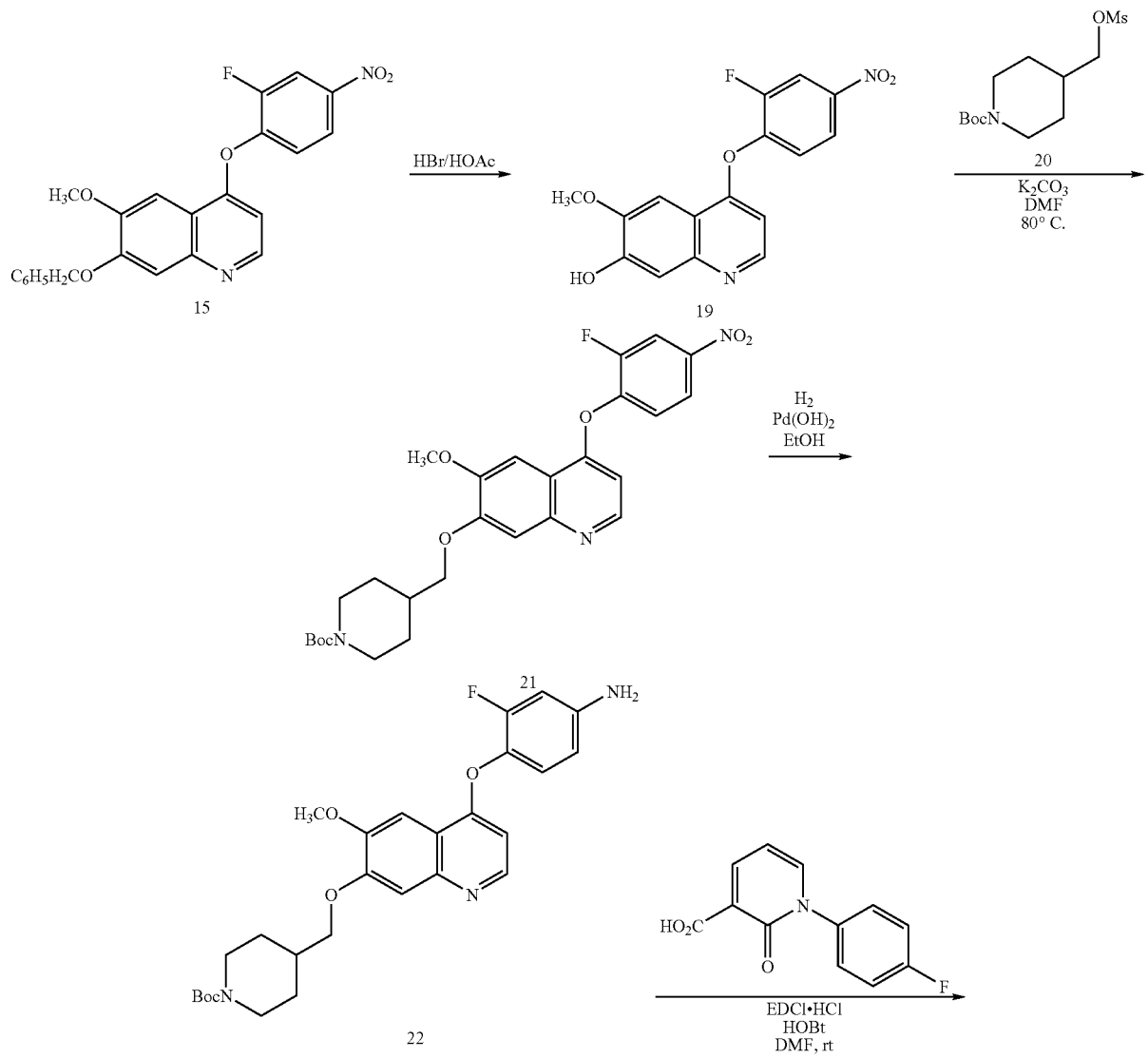

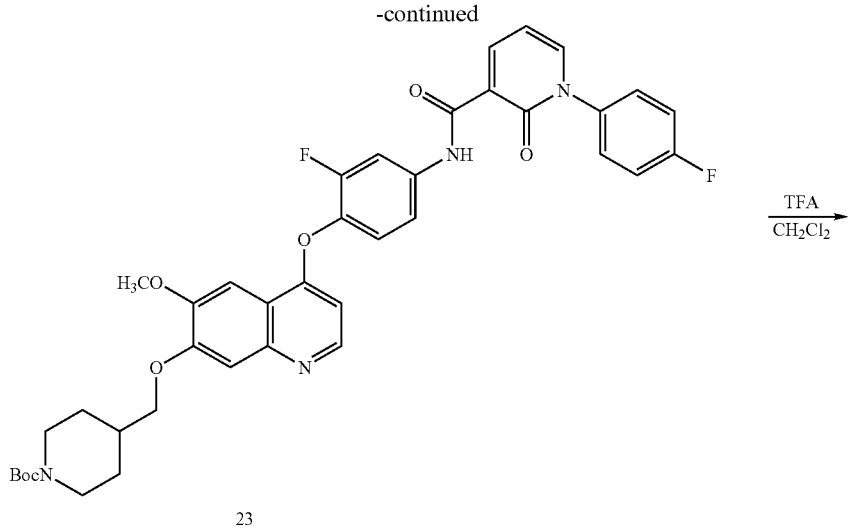
23
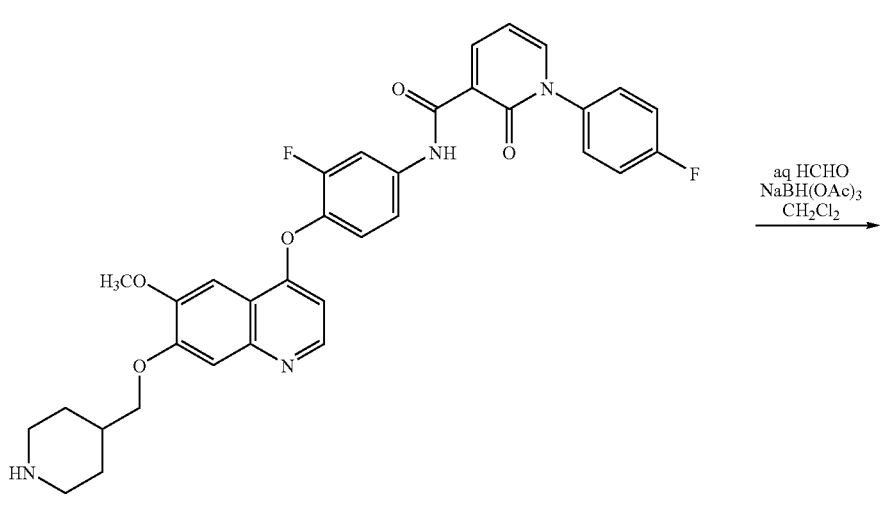
24
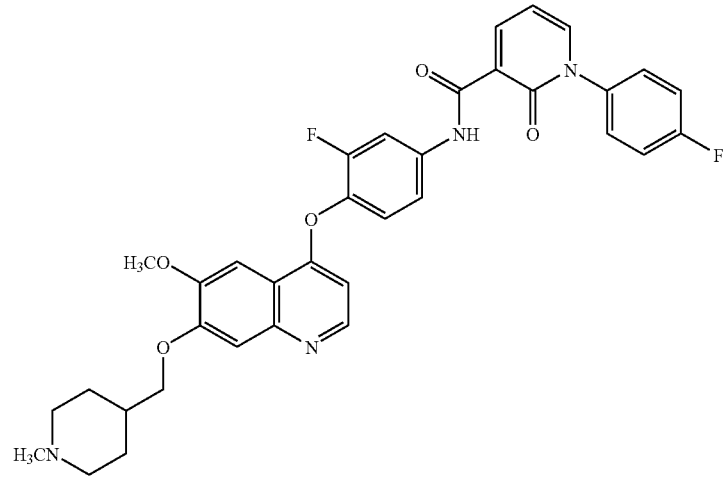
25

Quinoline analogue containing pyridine N-oxide 29 was prepared by the coupling of quinoline 5 with pyridine N-oxide 28 (Scheme 4). Pyridine N-oxide 28 was synthesized by Pd-mediated coupling of 6-bromopicolinic acid 26 with 2-(4-fluorophenyl)-5,5-dimethyl-1,3,2-dioxaborinane (Wako Pure Chemical Industries, Ltd) followed by oxidation using mCPBA.

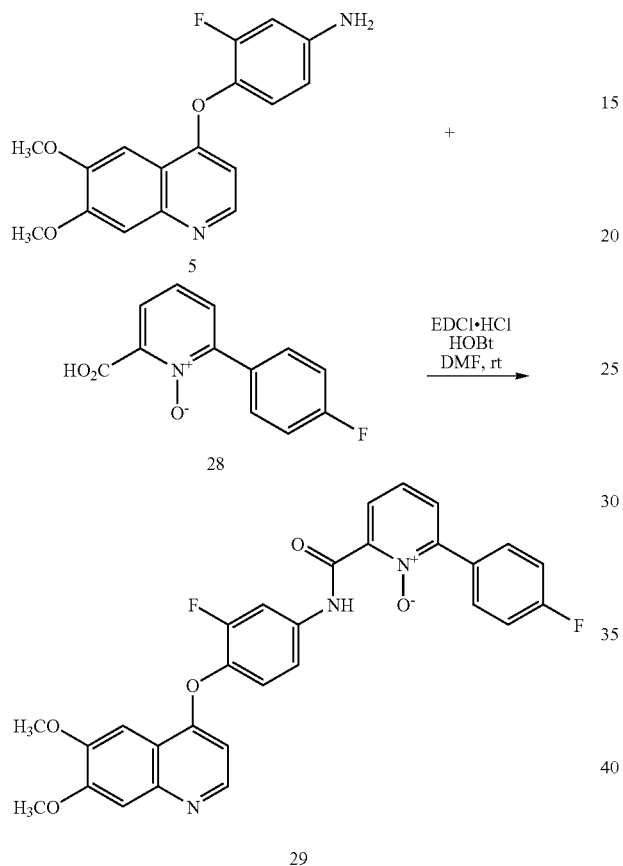

-continued

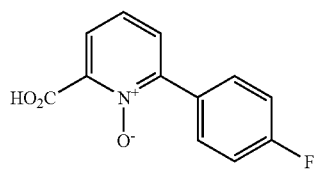

Quinoline analogue containing 4-pyridone moiety 34 can be prepared by coupling of 4-pyridone acid 33 with quinoline 5 (Scheme 5). 4-Pyridone acid 33 was obtained from 3,5-dibromo-4-hydroxypyridine 30 (*Synthesis*, 2001, No. 14, 2175-2179, incorporated by reference) which reacted with benzaldehyde after metallation 10 followed by reduction of the hydroxyl of 31 and carboxylation of metallated 32 with carbon dioxide.

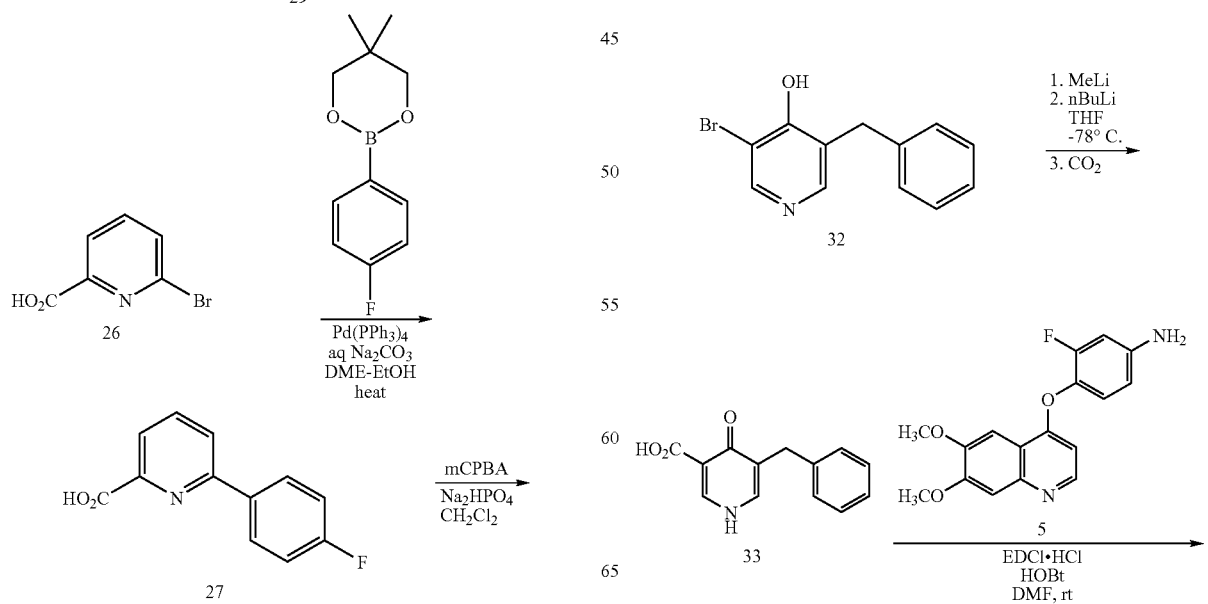

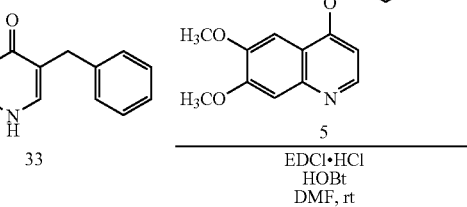

EXAMPLES

The following examples and preparations describe the manner and process of making and using the invention and are illustrative rather than limiting. It should be understood that there may be other embodiments which fall within the spirit and scope of the invention as defined by the claims appended hereto.

Example 1

N-(4-(6,7-Dimethoxyquinolin-4-yloxy)-3-fluorophenyl)-1-(4-fluorophenyl)-2-oxo-1,2-dihydropyridine-3-carboxamide

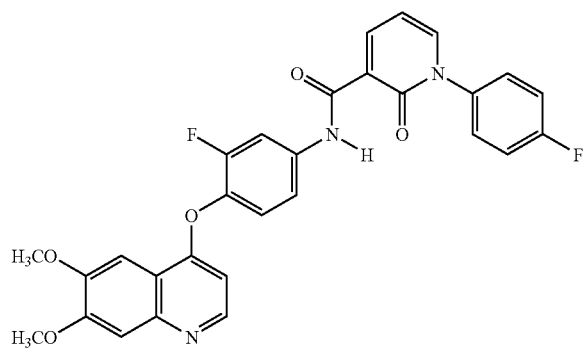

A) 6,7-Dimethoxyquinolin-4(1H)-one

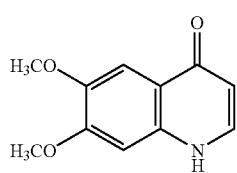

To a solution of 1-(2-amino-4,5-dimethoxyphenyl)ethanone (9.80 g, 50 mmol, Lancaster Synthesis LTD) in DME (300 mL) at rt was added NaOMe (15.0 g, 278 mmol), and the mixture was stirred for 30 minutes at rt. To this mixture was added ethyl formate (25 mL) dropwise with stirring at rt. After an hour the reaction was quenched by adding aq HCl (50 mL of 2N HCl), stirred for 10 minutes and the precipitate was filtered, washed with a small amount of H$_2$O and EtOAc to obtain the 1$^{st}$ crop of product. To the filtrate solution was added EtOAc (200 mL), the EtOAc layer was separated, the aqueous layer was washed with EtOAc (200 mL), and the combined EtOAc solution was dried over MgSO$_4$, concentrated in vacuo and the residue was triturated with a small amount of CH$_3$OH/EtOAc to obtain the 2$^{nd}$ crop of product. The solids of 1$^{st}$ crop and 2$^{nd}$ crop were combined, mixed with water (100 mL), stirred for 10 minutes, the solid was filtered and dried to obtain the product (9.75 g, 95%) as a white solid. $^1$H NMR (DMSO-d$_6$) δ 8.50 (s, 1H), 7.75 (d, 1H, J=4.2 Hz), 7.42 (s, 1H), 7.08 (s, 1H), 5.91 (d, 1H, J=4.2 Hz), 3.83 (s, 3H), 3.80 (s, 3H).

B) 4-(2-Fluoro-4-nitrophenoxy)-6,7-dimethoxyquinoline

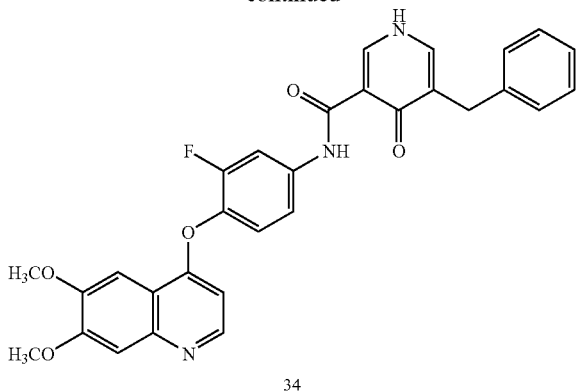

A mixture of 6,7-dimethoxyquinolin-4(1H)-one (7.9 g, 38.5 mmol), Cs$_2$CO$_3$ (15.4 g) in DMF (55 mL) and CH$_3$CN (80 mL) was stirred for 30 min. at rt. To this mixture was added 3,4-difluoronitrobenzene (6.5 g, 40.9 mmol), and the reaction mixture was stirred over the weekend at rt. To the reaction mixture was added H$_2$O (100 mL), stirred for 10 minutes and the precipitate was filtered, washed with a small amount of H$_2$O to obtain the 1$^{st}$ crop of solid. To the filtrate solution was added EtOAc (200 mL), the EtOAc layer was separated, the aqueous layer was washed with EtOAc (200 mL), and the combined EtOAc solution was dried over MgSO$_4$, concentrated in vacuo to obtain the 2$^{nd}$ crop of solid. The solids of first crop and second crop were combined which was a mixture of O- and N-alkylation products. The mixture of solid product was digested in CHCl$_3$ (35 mL) and DMF (5 mL), and the undissolved solid was filtered which was an N-alkylation product. The filtrate solution was passed through a flash column on SiO$_2$ eluting with 5% MeOH in CH$_2$Cl$_2$ to obtain the desired O-alkylation product (6.2 g, 47%) as a light yellow solid. $^1$H NMR (CDCl$_3$) δ 8.59 (d, 1H, J=5.0 Hz), 8.19 (dd, 1H, J=9.3, 2.8 Hz), 8.14 (dd, 1H, J=8.8, 2.2 Hz), 7.45 (d, 2H, J=9.9 Hz), 7.34 (t, 1H, J=8.3 Hz), 6.55 (d, 1H, J=5.0 Hz), 4.06 (s, 3H), 4.04 (s, 3H).

C) 4-(6,7-Dimethoxyquinolin-4-yloxy)-3-fluorobenzenamine

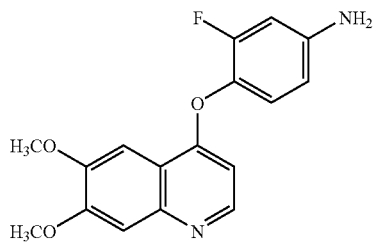

A mixture of 4-(2-fluoro-4-nitrophenoxy)-6,7-dimethoxyquinoline (612 mg, 1.8 mmol), Zn powder (2.0 g) and NH₄Cl (1.4 g) in MeOH (25 mL) and THF (25 mL) was heated at reflux temp. overnight with stirring. To this mixture was added DMF (45 mL) and water (20 mL), stirred for 10 minutes, and the solid was filtered. The filtrate solution was concentrated in vacuo, and the residue was purified by preparative HPLC to afford the product (230 mg, 41%) as a brown solid. $^1$H NMR (CDCl₃) δ 8.38 (d, 1H, J=5.5 Hz), 7.52 (s, 1H), 7.32 (s, 1H), 6.91 (t, 1H, J=8.8 Hz), 6.44 (dd, 1H, J=11.6, 2.2 Hz), 6.38 (dd, 1H, J=8.2, 2.2 Hz), 6.32 (d, 1H, J=5.0 Hz), 3.94 (s, 3H), 3.92 (s, 3H).

D) Methyl 1-(4-fluorophenyl)-2-oxo-1,2-dihydropyridine-3-carboxylate

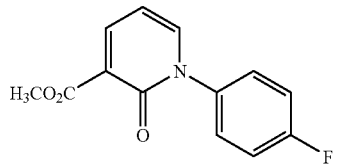

To a solution of methyl 2-oxo-2H-pyran-3-carboxylate (10.0 g, 65 mmol, Aldrich) in DMF (80 mL) at ice bath temperature was added a solid of 4-fluoroaniline (7.21 g, 65 mmol), stirred for 15 min. and the reaction mixture was warmed to rt, stirred for 3 h at rt. To the 4-fluoroaniline adduct intermediate formed via Michael addition was added in situ solids of EDCI.HCl (14.8 g, 77 mmol) and DMAP (1.80 g) at rt. The reaction mixture was stirred at rt overnight. Most of DMF was removed in vacuo, and to the residue were added 1N aq HCl (150 mL) and EtOAc (400 mL), the EtOAc layer was separated, and the aqueous layer was washed with EtOAc (2×200 mL), the combined EtOAc layer was washed with brine (150 mL), dried over MgSO₄ and concentrated in vacuo. The residue was triturated with iPrOH (180 mL) to obtain the 1$^{st}$ crop of product (8.5 g) as a yellow solid. The mother liquor was concentrated, and the residue was triturated with a small amount of ether to obtain the 2$^{nd}$ crop of product (2.5 g, total 11 g, 68%). $^1$H NMR (CDCl₃) δ 8.23 (dd, 1H, J=7.2, 2.2 Hz), 7.57 (dd, 1H, J=6.6, 1.7 Hz), 7.32-7.34 (m, 2H), 7.17 (t, 2H, J=8.8 Hz), 6.32 (t, 1H, J=7.1 Hz), 3.89 (s, 3H); MS(ESI⁺) m/z 248.2 (M+H)⁺.

E) 1-(4-Fluorophenyl)-2-oxo-1,2-dihydropyridine-3-carboxylic acid

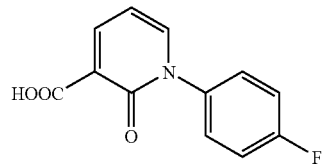

A mixture of 2-oxo-dihydropyridine ester (2.45 g, 12 mmol) and 6 N aq NaOH (2.5 mL) in methanol (60 mL) was stirred at rt for 4 h. To the reaction mixture was added conc HCl (1 mL) slowly with stirring at rt, and the precipitated solid was filtered, washed with a small amount water and dried to obtain the first crop of the desired acid product (2.1 g) as a yellow solid. The filtrate solution was concentrated, and the residue was mixed with water (50 mL) and it was washed with EtOAc (2×30 mL), EtOAc layer was dried over MgSO₄, and concentrated in vacuo. The residue was triturated with a small amount of ether to obtain the second crop of acid product (195 mg, total 2.295 g, 82%). $^1$H NMR (DMSO-d₆) δ 8.47 (dd, 1H, J=7.2, 2.2 Hz), 8.19 (dd, 1H, J=6.6, 1.7 Hz), 7.62-7.60 (m, 2H), 7.42 (t, 2H, J=8.8 Hz), 6.78 (t, 1H, J=7.1 Hz); MS(ESI⁺) m/z 234.2 (M+H)⁺.

F) N-(4-(6,7-Dimethoxyquinolin-4-yloxy)-3-fluorophenyl)-1-(4-fluorophenyl)-2-oxo-1,2-dihydropyridine-3-carboxamide To a mixture of 1-(4-fluorophenyl)-2-oxo-1,2-dihydropyridine-3-carboxylic acid (45 mg, 0.19 mmol), HOBt (20 mg) and EDCI.HCl (80 mg, 0.31 mmol) in DMF (2.5 mL) was added 4-(6,7-dimethoxyquinolin-4-yloxy)-3-fluorobenzenamine (56 mg, 0.18 mmol) at rt, and the reaction mixture was stirred over the weekend at rt. It was directly purified by preparative HPLC to afford the product (35 mg, 30%) as a beige-colored TFA salt solid. $^1$H NMR (CD₃OD) δ 12.21 (s, 1H), 8.60 (dd, 2H, J=9.9, 1.6 Hz), 8.01 (d, 1H, J=12.6 Hz), 7.90 (dd, 1H, J=7.6, 1.6 Hz), 7.74 (s, 1H), 7.45-7.37 (m, 5H), 7.24 (t, 2H, J=8.2 Hz), 6.89 (d, 1H, J=6.6 Hz), 6.65 (t, 1H, J=6.6 Hz), 4.03 (s, 3H), 4.00 (s, 3H); MS(ESI⁺) m/z 530.2 (M+H)⁺.

Example 2

N-(3-Fluoro-4-(7-hydroxy-6-methoxyquinolin-4-yloxy)phenyl)-1-(4-fluorophenyl)-2-oxo-1,2-dihydropyridine-3-carboxamide

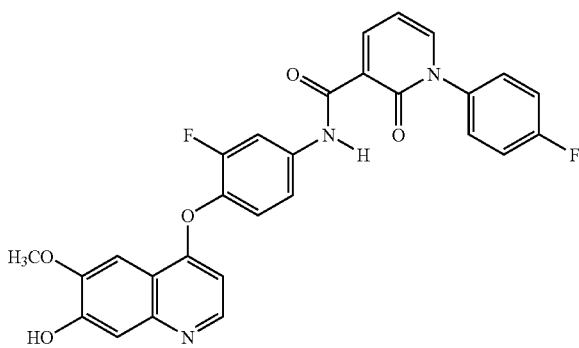

A) 1-(4-(Benzyloxy)-5-methoxy-2-nitrophenyl)ethanone

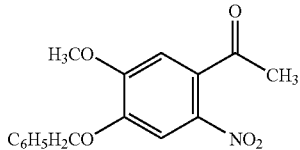

To a solution of 1-(4-(benzyloxy)-3-methoxyphenyl)ethanone (5.0 g, 19.5 mmol, Alfa Aesar Company) in dichloromethane (75 mL) at ice bath temp. was added slowly HNO$_3$ (1.5 mL of 90% nitric acid) followed by conc H$_2$SO$_4$ (1.8 mL of 96.2% acid) at 0° C. with stirring. After 1 h at 0° C. additional HNO$_3$ (0.5 mL) was added and the reaction mixture was stirred for 20 minutes at 0° C. To the reaction mixture was added dichloromethane (25 mL) and the mixture was poured into water (60 mL), the organic layer was separated which was washed with water (2×60 mL) followed by aq NaHCO$_3$ (2×60 mL), dried over Na$_2$SO$_4$ and concentrated in vacuo. The residue was mixed with DMF (~3 mL) and ether (70 mL), stirred for a while and the solid was filtered, washed with a small amount of ether and dried to obtain the desired product (3.6 g, 61%) as a yellow solid. $^1$H NMR (CDCl$_3$) δ 7.64 (s, 1H), 7.42-7.35 (m, 5H), 6.76 (s, 1H), 5.21 (s, 2H), 3.93 (s, 3H), 2.48 (s, 3H).

B) 1-(2-Amino-4-(benzyloxy)-5-methoxyphenyl)ethanone

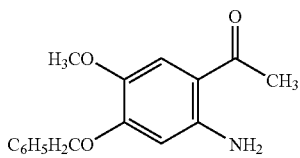

A mixture of 1-(4-(benzyloxy)-5-methoxy-2-nitrophenyl)ethanone (3.6 g, 12 mmol), iron powder (4.5 g) and ammonium formate (5.5 g) in toluene (50 mL) and water (50 mL) was heated at reflux temp. for 2 days with stirring. To this mixture was added EtOAc (100 mL), stirred for 20 minutes, the solid was filtered through a celite bed and washed with EtOAc (150 mL). The EtOAc layer was separated from the filtrate solution, washed with water (2×100 mL), dried over MgSO$_4$ and concentrated in vacuo to afford the product (2.80 g, 86%) as a beige-colored solid. $^1$H NMR (CDCl$_3$) δ 7.41-7.30 (m, 5H), 7.13 (s, 1H), 6.15 (br s, 2H), 6.10 (s, 1H), 5.13 (s, 2H), 3.84 (s, 3H), 2.51 (s, 3H).

C) 7-(Benzyloxy)-6-methoxyquinolin-4(1H)-one

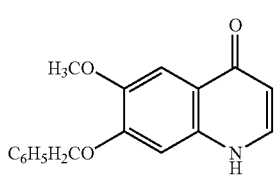

To a solution of 7-(benzyloxy)-6-methoxyquinolin-4(1H)-one (2.65 g, 9.8 mmol) in DME (50 mL) at rt was added NaOMe (4.65 g, 86 mmol), and the mixture was stirred for 30 minutes at rt. To this mixture was added ethyl formate (5 mL) dropwise with stirring at rt. After 90 minutes the reaction mixture was acidified to neutral with aq HCl, stirred for 20 minutes and the precipitate was filtered, washed with a small amount of H$_2$O and ether to obtain the product (1.05 g, 38%) as a beige-colored solid. $^1$H NMR (DMF-d7) δ 8.45 (d, 1H, J=5.0 Hz), 7.73-7.41 (m, 7H), 7.06 (s, 1H), 5.35 (s, 2H), 4.01 (s, 3H).

D) 7-(Benzyloxy)-4-(2-fluoro-4-nitrophenoxy)-6-methoxyquinoline

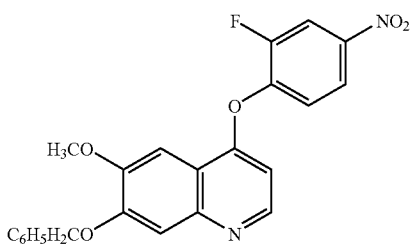

A mixture of 7-(benzyloxy)-6-methoxyquinolin-4(1H)-one (4.4 g, 15.6 mmol), Cs$_2$CO$_3$ (9.0 g) in DMF (40 mL) and CH$_3$CN (40 mL) was stirred for 30 minutes at rt. To this mixture was added 3,4-difluoronitrobenzene (2.5 g, 15.7 mmol), and the reaction mixture was stirred at rt overnight. The reaction product was a mixture of O- and N-alkylation products. It was mostly concentrated in vacuo, EtOAc (200 mL) and water (50 mL) were added to the residue, EtOAc layer was separated, dried over MgSO$_4$ and concentrated in vacuo. The residue was purified by flash column chromatography on silica gel eluting with hexane:EtOAc:MeOH/800:200:40, and then 700:300:40 to obtain the desired O-alkylation product (3.0 mg, 46%) as a white solid. $^1$H NMR (CDCl$_3$) δ 8.73 (d, 1H, J=6.0 Hz), 8.29-8.26 (m, 2H), 8.08 (s, 1H), 7.60-7.35 (m, 7H), 6.67 (d, 1H, J=6.6 Hz), 5.42 (s, 2H), 4.10 (s, 3H); MS(ESI$^+$) m/z 421.3 (M+H)$^+$.

E) 4-(7-(Benzyloxy)-6-methoxyquinolin-4-yloxy)-3-fluorobenzenamine

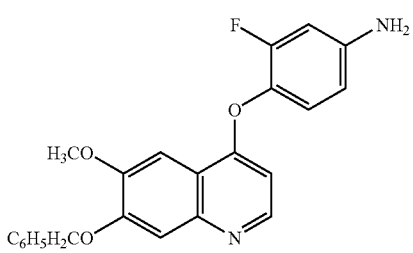

A mixture of 7-(benzyloxy)-4-(2-fluoro-4-nitrophenoxy)-6-methoxyquinoline (125 mg, 0.3 mmol) and PtO$_2$ in EtOAc (15 mL) was stirred at rt under 1 atm of H$_2$ gas for 2 h. Toluene (4 mL) and MeOH (5 mL) were added to the reaction mixture, stirred for 20 minutes, filtered the catalyst, and the filtrate solution was concentrated in vacuo to obtain the product (117 mg, 100%) as a white solid. $^1$H NMR (DMF-d7) δ 8.52 (d, 1H, J=5.0 Hz), 7.68-6.67 (m, 12H), 6.48 (d, 1H, J=5.0 Hz), 5.38 (s, 2H), 4.02 (s, 3H).

F) N-(4-(7-(Benzyloxy)-6-methoxyquinolin-4-yloxy)-3-fluorophenyl)-1-(4-fluorophenyl)-2-oxo-1,2-dihydropyridine-3-carboxamide

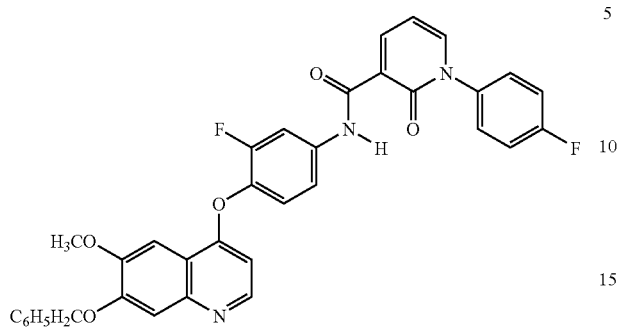

To a mixture of 1-(4-fluorophenyl)-2-oxo-1,2-dihydropyridine-3-carboxylic acid (74 mg, 0.32 mmol), HOBt (16 mg) and EDCI.HCl (65 mg, 0.34 mmol) in DMF (3 mL) was added a solution of 4-(6,7-dimethoxyquinolin-4-yloxy)-3-fluorobenzenamine (120 mg, 0.31 mmol) in DMF (3 mL) at rt, and the reaction mixture was stirred overnight at rt. It was directly purified by preparative HPLC to afford the product (46 mg, 20%) as a white TFA salt solid. $^1$H NMR (DMF-d7) δ 12.22 (s, 1H), 8.71 (d, 1H, J=6.0 Hz), 8.59 (d, 1H, J=7.2 Hz), 8.14-7.31 (m, 15H), 6.84 (d, 1H, J=5.5 Hz), 6.72 (t, 1H, J=7.2 Hz), 5.35 (s, 2H), 4.02 (s, 3H); MS(ESI$^+$) m/z 606.3 (M+H)$^+$.

G) N-(3-Fluoro-4-(7-hydroxy-6-methoxyquinolin-4-yloxy)phenyl)-1-(4-fluorophenyl)-2-oxo-1,2-dihydropyridine-3-carboxamide A mixture of N-(4-(7-(benzyloxy)-6-methoxyquinolin-4-yloxy)-3-fluorophenyl)-1-(4-fluorophenyl)-2-oxo-1,2-dihydropyridine-3-carboxamide trifluoroacetic acid salt (40 mg, 0.056 mmol) and HBr in HOAc (3 mL of 33% solution) was allowed to stay at rt for 70 minutes. Ether (25 mL) was added to the reaction mixture, stirred for 20 minutes, and the solid was filtered and dried to obtain the product (17 mg, 59%) as a light brown solid. $^1$H NMR (DMF-d7) δ 12.35 (s, 1H), 8.94 (d, 1H, J=6.6 Hz), 8.70 (d, 1H, J=7.7 Hz), 8.23-7.50 (m, 12H), 7.12 (d, 1H, J=6.6 Hz), 6.84 (m, 1H), 4.17 (s, 3H); MS(ESI$^+$) m/z 516.2 (M+H)$^+$.

Example 3

N-(3-Fluoro-4-(6-methoxy-7-(piperidin-4-ylmethoxy)quinolin-4-yloxy)phenyl)-1-(4-fluorophenyl)-2-oxo-1,2-dihydropyridine-3-carboxamide

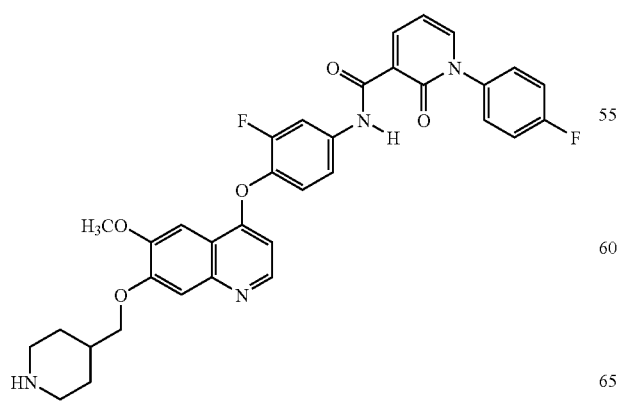

A) 4-(2-Fluoro-4-nitrophenoxy)-6-methoxyquinolin-7-ol

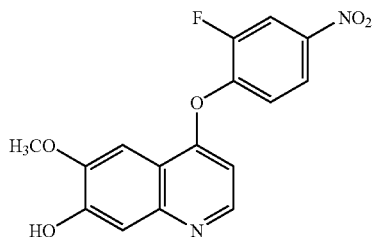

A mixture of 7-(benzyloxy)-4-(2-fluoro-4-nitrophenoxy)-6-methoxyquinoline (2.20 g, 5.24 mmol) and HBr in HOAc (3 mL of 33% solution) was allowed to stay at rt for 4 h. Ether (35 mL) was added to the reaction mixture, stirred for 20 minutes, and the solid was filtered and dried to obtain the product (2.15 g, 100%) as a beige-colored HBr salt solid. $^1$H NMR (CD$_3$OD) δ 8.69 (d, 1H, J=6.6 Hz), 8.41 (dd, 1H, J=9.9, 2.8 Hz), 8.33 (dd, 1H, J=8.8, 1.7 Hz), 7.84 (m, 2H), 7.43 (s, 1H), 7.05 (d, 1H, J=6.1 Hz), 4.13 (s, 3H).

B) tert-Butyl 4-((methylsulfonyloxy)methyl)piperidine-1-carboxylate

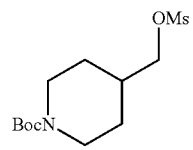

To a mixture of tert-butyl 4-(hydroxymethyl)piperidine-1-carboxylate (Aldrich) (4.30 g, 20 mmol) and Et$_3$N (5 mL) in THF (60 mL) at 0° C. was added MeSO$_2$Cl (1.6 mL) dropwise with stirring. After 2.5 h EtOAc (160 mL) and water (50 mL) were added to the reaction mixture, the EtOAc layer was separated, washed with 1N HCl (30 mL), dried over MgSO$_4$, concentrated in vacuo to obtain the product (5.8 g, 98.9%) as a low melting white solid. This material was used directly for the next step without any further purification. $^1$H NMR (CDCl$_3$) δ 4.20 (m, 2H), 4.04 (d, 2H, J=6.1 Hz), 2.99 (s, 3H), 2.68 (m, 2H), 2.01-1.70 (m, 3H), 1.43 (s, 9H), 1.20 (m, 2H).

C) tert-Butyl 4-((4-(2-fluoro-4-nitrophenoxy)-6-methoxyquinolin-7-yloxy)methyl)piperidine-1-carboxylate

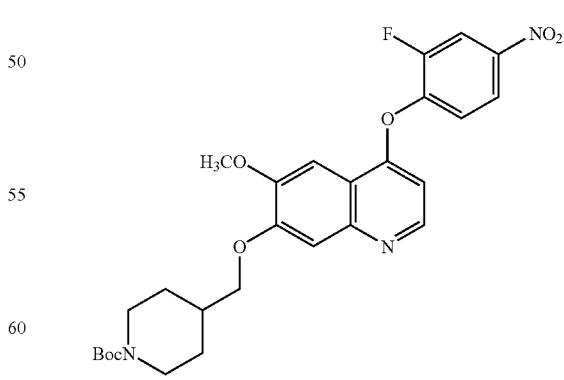

To a mixture of 4-(2-fluoro-4-nitrophenoxy)-6-methoxyquinolin-7-ol HBr salt (1.0 g, 2.4 mmol) and K$_2$SO$_3$ (2.5 g) in DMF (15 mL) at rt was added tert-butyl 4-((methylsulfonyloxy)methyl)piperidine-1-carboxylate (1.0 g, 3.4 mmol, and the reaction mixture was heated at 80-85° C. for 4 h. This mixture was directly purified by flash column chromatography on silica gel eluting with hexane:EtOAc/600:400, and then 300:700 to obtain the desired product (786 mg, 62%) as a glassy solid material. $^1$H NMR (CDCl$_3$) δ 8.57 (d, 1H, J=5.0 Hz), 8.20 (dd, 1H, J=9.9, 2.8 Hz), 8.13 (dd, 1H, J=8.8, 1.7 Hz), 7.43 (d, 2H, J=2.2 Hz), 7.33 (t, 1H, J=7.7 Hz), 6.54 (d, 1H, J=5.0 Hz), 4.20 (m, 2H), 4.04 (d, 2H, J=6.6 Hz), 4.00 (s, 3H), 2.77 (m, 2H), 2.19-1.89 (m, 3H), 1.47 (s, 9H), 1.34 (m, 2H).

D) tert-Butyl 4-((4-(4-amino-2-fluorophenoxy)-6-methoxyquinolin-7-yloxy)methyl)piperidine-1-carboxylate

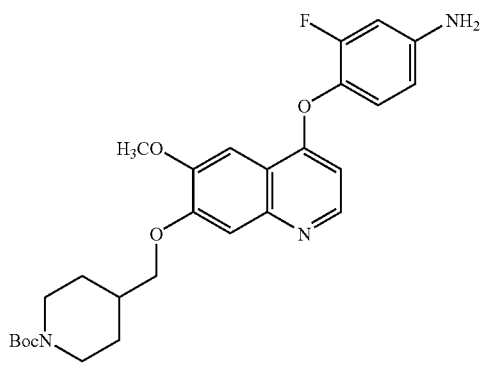

A mixture of tert-butyl 4-((4-(2-fluoro-4-nitrophenoxy)-6-methoxyquinolin-7-yloxy)methyl)piperidine-1-carboxylate (100 mg, 0.19 mmol) and 10% Pd(OH)$_2$ (25 mg) on carbon in EtOH (20 mL) was stirred at rt under 1 atm of H$_2$ gas for 1.5 h. Toluene (4 mL) and MeOH (5 mL) were added to the reaction mixture, stirred for 20 minutes, filtered the catalyst, and the filtrate solution was concentrated in vacuo and purification by preparative HPLC afforded the desired product as a glassy brown TFA salt (40 mg, 41%). $^1$H NMR (CDCl$_3$) δ 8.61 (d, 1H, J=5.0 Hz), 7.73 (s, 1H), 7.64 (s, 1H), 7.09 (t, 1H, J=8.8 Hz), 6.76-6.64 (m, 3H), 4.19 (d, 2H, J= 11.5 Hz), 4.10 (d, 2H, J-6.0 Hz), 4.08 (s, 3H), 2.80 (m, 2H), 2.15-1.88 (m, 3H), 1.48 (s, 9H), 1.35 (m, 2H); MS(ESI$^+$) m/z 498.3 (M+H)$^+$.

E) tert-Butyl 4-((4-(2-fluoro-4-(1-(4-fluorophenyl)-2-oxo-1,2-dihydropyridine-3-carboxamido)phenoxy)-6-methoxyquinolin-7-yloxy)methyl)piperidine-1-carboxylate

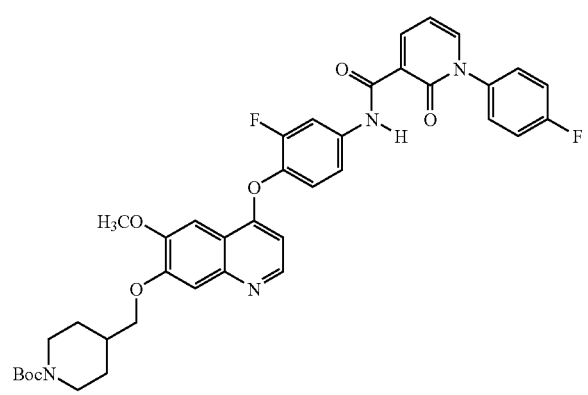

To a mixture of 1-(4-fluorophenyl)-2-oxo-1,2-dihydropyridine-3-carboxylic acid (15 mg, 0.06 mmol), HOBt (10 mg) and EDCI.HCl (20 mg, 0.10 mmol) in DMF (2 mL) was added a solution of tert-butyl 4-((4-(4-amino-2-fluorophenoxy)-6-methoxyquinolin-7-yloxy)methyl)piperidine-1-carboxylate (35 mg, 0.07 mmol) in DMF (1 mL) at rt, and the reaction mixture was stirred overnight at rt. It was directly purified by preparative HPLC to afford the product (24 mg, 56%) as a white TFA salt solid. $^1$H NMR (CDCl$_3$) δ 12.16 (s, 1H), 8.75 (d, 1H, J=7.7 Hz), 8.64 (d, 1H, J=5.5 Hz), 8.05 (d, 1H, J=12.1 Hz), 7.83 (s, 1H), 7.67-7.24 (m, 8H), 6.72 (d, 1H, J=6.1 Hz), 6.65 (t, 1H, J=6.6 Hz), 4.22-4.11 (m, 2H), 4.07 (s, 3H), 3.48 (s, 2H), 2.78 (m, 2H), 2.13 (m, 1H), 1.87 (m, 2H), 1.47 (s, 9H), 1.35 (m, 2H).

F) N-(3-Fluoro-4-(6-methoxy-7-(piperidin-4-ylmethoxy)quinolin-4-yloxy)phenyl)-1-(4-fluorophenyl)-2-oxo-1,2-dihydropyridine-3-carboxamide A mixture of tert-butyl 4-((4-(4-amino-2-fluorophenoxy)-6-methoxyquinolin-7-yloxy)methyl)piperidine-1-carboxylate (24 mg, 0.037 mmol) and trifluoroactic acid (0.5 mL) in CH$_2$Cl$_2$ was stirred at rt for 3.5 h, concentrated in vacuo and purification by preparative HPLC afforded the desired product as a white TFA salt solid (25 mg, 93%). $^1$H NMR (CDCl$_3$) δ 12.15 (s, 1H), 9.72 (br s, 1H), 9.15 (br s, 1H), 8.76 (dd, 1H, J=7.2, 1.7 Hz), 8.61 (d, 1H, J=6.6 Hz), 8.06 (d, 1H, J=9.9 Hz), 7.67-7.25 (m, 8H), 6.72 (d, 1H, J=6.1 Hz), 6.65 (t, 1H, J=6.6 Hz), 4.24 (m, 2H), 4.07 (s, 3H), 3.54 (br s, 2H), 3.00 (m, 2H), 2.30 (m, 1H), 2.15-1.83 (m, 4H); MS(ESI$^+$) m/z 613.4 (M+H)$^+$.

Example 4

N-(3-Fluoro-4-(6-methoxy-7-((1-methylpiperidin-4-yl)methoxy)quinolin-4-yloxy)phenyl)-1-(4-fluorophenyl)-2-oxo-1,2-dihydropyridine-3-carboxamide

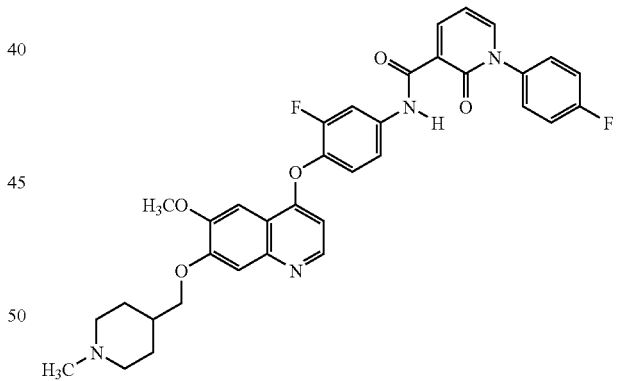

To a mixture of N-(3-fluoro-4-(6-methoxy-7-(piperidin-4-ylmethoxy)quinolin-4-yloxy)phenyl)-1-(4-fluorophenyl)-2-oxo-1,2-dihydropyridine-3-carboxamide TFA salt (22 mg, 0.030 mmol) and NaBH(OAc)$_3$ (40 mg) in CH$_2$Cl$_2$ was added HCHO (0.1 mL of 33% solution) and the reaction mixture was stirred at rt for 6 h. Direct purification by preparative HPLC afforded the desired product as a white TFA salt solid (11 mg, 50%). $^1$H NMR (CDCl$_3$) δ 12.16 (s, 1H), 8.77 (dd, 1H, J=7.7, 2.2 Hz), 8.55 (d, 1H, J=6.1 Hz), 8.08 (d, 1H, J=1.6 Hz), 8.06 (dd, 1H, J= 12.1, 1.6 Hz), 7.64-7.27 (m, 8H), 6.71 (d, 1H, J=6.6 Hz), 6.66 (t, 1H, J=6.6 Hz), 4.27 (d, 2H, J=5.5 Hz), 4.07 (s, 3H), 3.66 (d, 2H, J=12.1 Hz), 2.81 (s, 3H), 2.87-1.97 (m, 7H); MS(ESI$^+$) m/z 627.4 (M+H)$^+$.

Example 5

N-(4-(6,7-Dimethoxyquinolin-4-yloxy)-3-fuorophenyl)-6-(4-fluorophenyl)picolin-N-oxide-amide

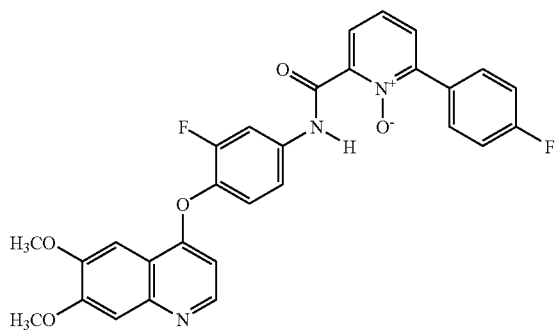

A) 6-(4-Fluorophenyl)picolinic acid

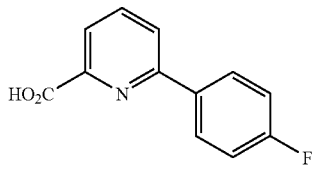

A solution of 6-bromopicolinic acid (Aldrich) (2.02 g, 10 mmol) in DME containing 4 mL of 10% aq $Na_2CO_3$ was purged with Ar gas. To this mixture was added $Pd(PPh_3)_4$ followed by 2-(4-fluorophenyl)-5,5-dimethyl-1,3,2-dioxaborinane (2.40 g, 11.5 mmol, Wako Pure Chemical Industries, Ltd) and EtOH (20 mL), and the mixture was purged with Ar gas. The reaction mixture was heated at 100° C. for 2.5 h in a sealed tube. Additional 2-bromopicolinic acid (900 mg) and Pd (OAc)$_2$ was added, and after purging with Ar gas it was heated at 100° C. for 4.5 h. Trifluoroacteic acid (20 mL) was added to the reaction mixture, concentrated and MeOH (150 mL) was added to the residue. The insoluble material was filtered, and the filtrate solution was concentrated. Purification by flash column on silica gel eluting with EtOAc/MeOH//900:100 followed by EtOAc/MeOH/HOAc//700:1500:50 provided the desired product (1.0 g, 40% based on borinane starting material) as a white solid. $^1$H NMR (CD$_3$OD) δ 8.01 (d, 1H, J=7.7 Hz), 7.94-7.87 (m, 3H), 7.73 (d, 1H, J=7.7 Hz), 7.13 (t, 2H, 8.8 Hz); MS(ESI$^+$) m/z 234 (M+H)$^+$.

B) 6-(4-Fluorophenyl)picolinic acid-N-oxide

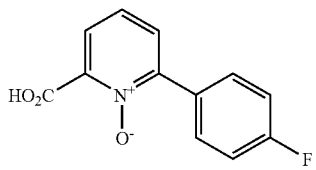

A mixture of picolinic acid derivative (1.0 g, 4.6 mmol), $Na_2HPO_4$ (1.2 g) and mCPBA (1.1 g, ~70% from Aldrich) in $CH_2ClCH_2Cl$ (30 mL) was stirred at rt for 2 h. Additional $Na_2HPO_4$ (0.8 g) and mCPBA (1.0 g, ~70% from Aldrich) was added to the reaction mixture and it was stirred for 3 h at rt. Another $Na_2HPO_4$ (0.5 g) and mCPBA (0.5 g, ~70% from Aldrich) was added to the reaction mixture and it was stirred at rt overnight. Next morning CHCl$_3$ (160 mL) and 2N aq HCl (50 mL) were added to the reation mixture, the organic layer was separated, dried over MgSO$_4$ and concentrated. The residue was purified by flash column on silica gel eluting with EtOAc/MeOH/HOAc//700:240:60 to obtain the desired product contaminated by mCPBA. This impure material was purified by preparative HPLC to obtain the desired product (175 mg, 16%) as a white solid. $^1$H NMR (DMF-d7) 8.45 dd, 1H, J=8.3, 2.2 Hz), 8.15 (d, 1H, J=2.2 Hz), 8.13-8.00 (m, 4H), 7.45 (t, 2H, 8.7 Hz).

C) N-(4-(6,7-Dimethoxyquinolin-4-yloxy)-3-fluorophenyl)-6-(4-fluorophenyl)picolin-N-oxide-amide To a mixture of 6-(4-fluorophenyl)picolinic acid-N-oxide (45 mg, 0.19 mmol), HOBt (20 mg) and EDCI.HCl (40 mg, 0.21 mmol) in DMF (3 mL) was added a solid of 4-(6,7-dimethoxyquinolin-4-yloxy)-3-fluorobenzenamine (63 mg, 0.20 mmol) at rt, and the reaction mixture was stirred overnight at rt. It was directly purified by preparative HPLC to afford the product (39 mg, 32%) as a white TFA salt solid. $^1$H NMR (DMF-d7) δ 14.13 (s, 1H), 8.91 (d, 1H, J=6.1 Hz), 8.49 (d, 1H, J= 7.7 Hz), 8.25 (d, 1H, J=12.6 Hz), 8.03-7.69 (m, 8H), 7.44 (t, 2H, J=8.8 Hz), 7.08 (d, 1H, J=6.1 Hz), 4.16 (s, 3H), 4.14 (s, 3H); MS(ESI$^+$) m/z 530.2 (M+H)$^+$.

Example 6

5-Benzyl-N-(4-(6,7-dimethoxyquinolin-4-yloxy)-3-fluorophenyl)-4-oxo-1,4-dihydropyridine-3-carboxamide

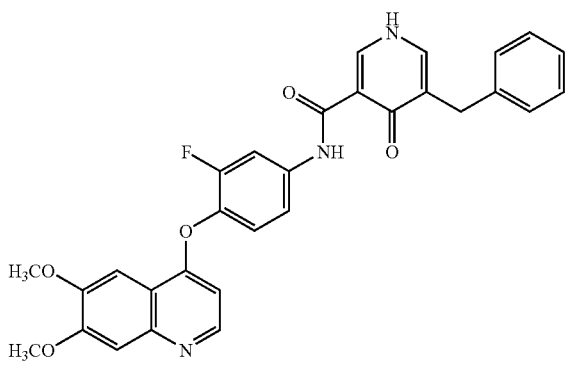

A) 3-Bromo-5-(hydroxy(phenyl)methyl)pyridin-4-ol

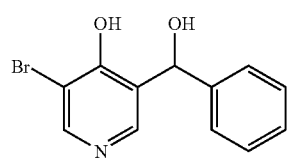

To a heterogeneous mixture of 3,5-dibromo-4-hydroxypyridine (2.53 g, 10 mmol, prepared following the procedure in Synthesis, 2001, No. 14, 2175-2179) in anhydrous THF (20 mL) at −78° C. under Ar-atm was added phenylmagnesium bromide solution (11 mL of 1 M solution in THF, 11 mmol). After stirring for 15 min. was added nBuLi solution (5.5 mL of 2 M solution in cyclohexane), and the reaction mixture was stirred for 15 minutes at −78° C. under Ar-atm. To this mixture benzaldehyde (2.15 mL, 21 mmol) was added and the reaction mixture was stirred for 2 h −78° C. under Ar-atm. The reaction mixture was quenched by adding HOAc (3 mL) and TFA (3 mL), concentrated and the residue was purified by flash column on silica gel eluting with hexane/EtOAc/MeOH//750:250:50 followed by hexane/EtOAc/MeOH/Et$_3$N//460:460:50:10 to obtain the desired product (2.85 g, 91%) as a white solid. $^1$H NMR (CD$_3$OD) δ 8.13 (s, 1H), 8.04 (s, 1H), 7.41-7.20 (m, 5H), 5.94 (s, 1H); MS(ESI$^+$) m/z 280, 282 (M+H)$^+$.

B) 3-Benzyl-5-bromopyridin-4-ol

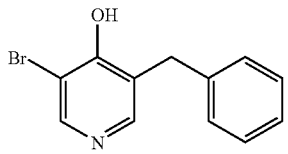

A mixture of 3-bromo-5-(hydroxy(phenyl)methyl)pyridin-4-ol (2.55 g, 91 mmol), TFA (16 mL) and Et$_3$SiH in CH$_2$Cl$_2$ (30 mL) at rt for 10 h. It was concentrated in vacuo and the residue was purified by flash column on silica gel eluting with hexane/EtOAc/MeOH//600:300:50 followed by hexane/EtOAc/MeOH//400:400:50:10 to obtain an impure product which was triturated with a small amount of MeOH and Et$_2$O to obtain the desired product (255 mg, 10%) as a white solid. $^1$H NMR (DMSO-d$_6$) δ 11.75 (br s, 1H), 8.13 (s, 1H), 7.54 (s, 1H), 7.26-7.14 (m, 5H), 2.49 (s, 2H).

C) 5-Benzyl-4-oxo-1,4-dihydropyridine-3-carboxylic acid

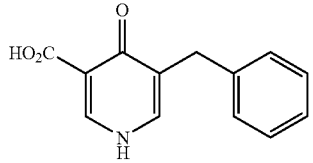

To a solution of 3-benzyl-5-bromopyridin-4-ol (220 mg, 0.83 mmol) in anhydrous THF (8 mL) at −78° C. under Ar-atm was added MeLi solution (0.61 mL of 1.5 M solution in THF, 0.92 mmol). After stirring for 5 minutes was added nBuLi solution (0.5 mL of 2 M solution in cyclohexane, 1.0 mmol), and the mixture was stirred for 15 minutes at −78° C. under Ar-atm. To this mixture carbon dioxide was bubbled through the solution for 20 minutes at −78° C. The reaction mixture was quenched by adding HOAc (2 mL), concentrated and the residue was purified by preparative HPLC to afford the desired product as a white TFA solid salt (100 mg, 35%). $^1$H NMR (DMF-d7) δ 12.99 (br s, 1H), 8.69 (s, 1H), 8.28 (s, 1H), 7.35-7.19 (m, 5H), 3.90 (s, 2H)); MS(ESI$^+$) m/z 230.1 (M+H)$^+$.

D) 5-Benzyl-N-(4-(6,7-dimethoxyquinolin-4-yloxy)-3-fluorophenyl)-4-oxo-1,4-dihydropyridine-3-carboxamide To a solution of 4-hydroxy-5-benzylnicotinic acid (35 mg, 0.15 mmol) and HOBt (30 mg) in DMF (2.5 mL) at rt is added EDCI.HCl (80 mg, 0.42 mmol) followed by 4-(6,7-dimethoxyquinolin-4-yloxy)-3-fluorobenzenamine (50 mg, 0.16 mmol), and the reaction mixture is stirred for 40 h at rt. Purification by preparative HPLC affords the desired product as a white TFA solid salt.

I claim:

1. A compound having the following Formula I, II or III:

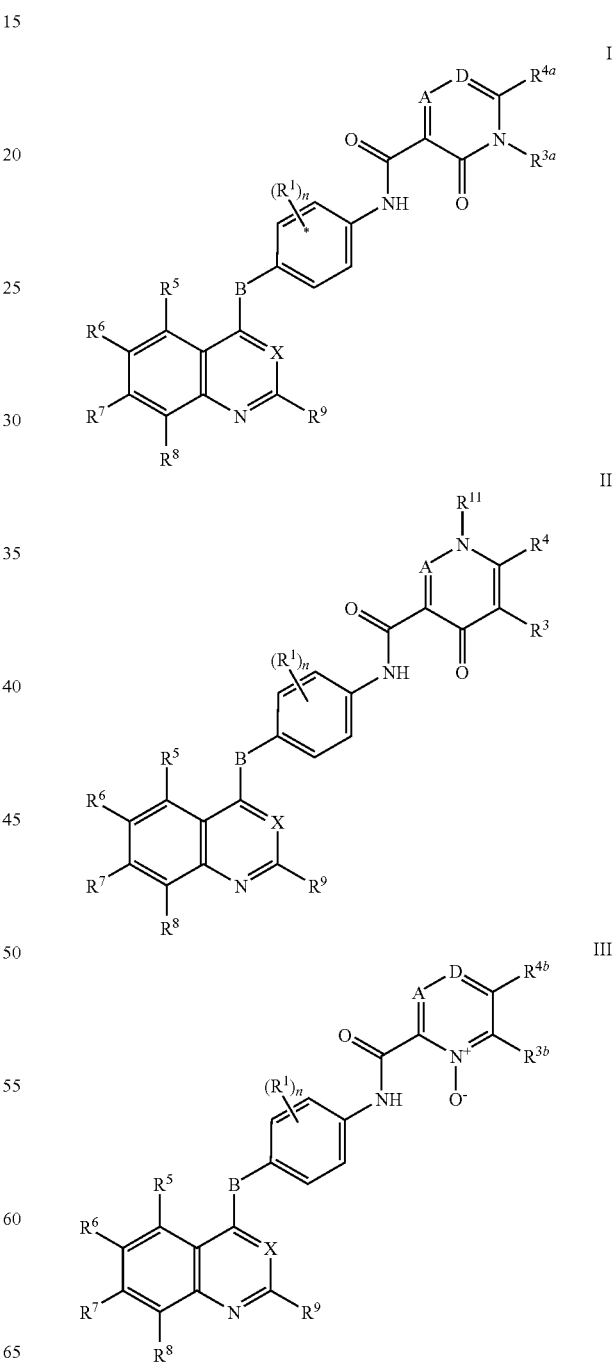

wherein:
X is —$CR^{12}$;
B is O;
A is —$CR^d$;
D is —$CR^e$;
l is 0 to 6;
n is 1;
each $R^1$ is independently H, halogen, cyano, $NO_2$, $OR^{13}$, $NR^{14}R^{15}$ alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, arylalkyl, substituted arylalkyl, heterocycloalkyl, or substituted heterocycloalkyl;
$R^3$, $R^{3b}$, $R^4$, $R^{4a}$, $R^{4b}$, $R^9$, $R^d$ and $R^e$ are independently H, alkyl, substituted alkyl, alkenyl, substituted alkenyl, alkynyl, substituted alkynyl, —CN, hydroxyl, halo, amino, alkylthio, alkoxy, aryl, heterocycloalkyl, aralkyl, alkylaryl, aminoalkylamino, or alkylaminoalkoxy;
$R^{3a}$ is H, alkyl, substituted alkyl, alkenyl, substituted alkenyl, alkynyl, substituted alkynyl, —CN, hydroxyl, amino, alkylthio, alkoxy, aryl, heterocycloalkyl, aralkyl, alkylaryl, aminoalkylamino, or alkylaminoalkoxy;
$R^5$, $R^6$, $R^7$, $R^8$ and $R^{12}$ are independently H, halogen, $NO_2$, cyano, —$OR^{13}$, —$NR^{14}R^{15}$, —$CO_2R^{16}$, —$C(O)NR^{14}R^{15}$, —$SO_2R^{16}$, —$SO_2NR^{14}R^{15}$, —$NR^{14}SO_2R^{15}$, —$NR^{14}C(O)R^{15}$, —$NR^{14}CO_2R^{15}$, —$CO(CH_2)_lR^{15}$, —$CONH(CH_2)_lR^{16}$, alkylaminoalkyl, alkylaminoalkynyl, $C_1$ to $C_6$ alkyl, substituted $C_1$ to $C_6$ alkyl, cycloalkyl, substituted cycloalkyl, alkenyl, substituted alkenyl, alkynyl, substituted alkynyl, hydroxyalkyl, aryl, substituted aryl, heteroaryl, substituted heteroaryl, arylalkyl, substituted arylalkyl, heterocycloalkyl, or substituted heterocycloalkyl;
$R^{11}$ is H, $C_1$ to $C_6$ alkyl, substituted $C_1$ to $C_6$ alkyl, $C_3$ to $C_7$ cycloalkyl, substituted $C_3$ to $C_7$ cycloalkyl, —$OR^{13}$, aryl, substituted aryl, heteroaryl, substituted $C_5$ to $C_{14}$ heteroaryl, arylalkyl, substituted arylalkyl, heteroarylalkyl, substituted heteroarylalkyl, heterocycloalkyl, substituted heterocycloalkyl, heterocycloalkylalkyl or substituted heterocycloalkylalkyl;
$R^a$, $R^{13}$, $R^{14}$, $R^{15}$ and $R^{16}$ are independently H, alkyl, substituted alkyl, cycloalkyl, substituted cycloalkyl, aryl, substituted aryl, arylalkyl, substituted arylalkyl, heteroaryl, substituted heteroaryl, heterocycloalkyl, or substituted heterocycloalkyl;
$R^b$ and $R^c$ are independently H, alkyl, substituted alkyl, cycloalkyl, substituted cycloalkyl, aryl, substituted aryl, heteroaryl, substituted heteroaryl, heterocycloalkyl, substituted heterocycloalkyl or taken together to form a carbocyclic or heterocyclic ring of 3 to 8 atoms.

2. The compound according to claim 1 wherein A is CH.

3. The compound according to claim 1 wherein D is CH.

4. The compound according to claim 1 wherein $R^{4a}$ or $R^d$ is hydroxyl, halo, $C_1$ to $C_4$ alkyl, CN, alkylthio, alkoxy, phenyl, amino, heterocycloalkyl, aminoalkylamino and alkylaminoalkoxy.

5. The compound according to claim 1 wherein $R^{3a}$ is phenyl.

6. The compound according to claim 1 wherein $R^3$ is benzyl.

7. The compound according to claim 1 wherein at least one of $R^6$ and $R^7$ is —OH, —$OCH_3$, or —$OCH_2$piperidine.

8. The compound according to claim 1 having Formula I, wherein $R^1$ is F, $R^{3a}$ is phenyl, $R^{4a}$ is H, and at least one of $R^6$ or $R^7$ is —OH, —$OCH_3$, or $OCH_2$piperidine.

9. The compound according to claim 1 having Formula III wherein $R_1$ is F, $R^3$ is benzyl, $R^4$ is H, and at least one of $R^6$ and $R^7$ is —$OCH_3$.

10. A pharmaceutical composition comprising a compound according to claim 1 in a pharmaceutically acceptable carrier.

11. A compound selected from the group consisting of:
N-(4-(6,7-Dimethoxyquinolin-4-yloxy)-3-fluorophenyl)-1-(4-fluorophenyl)-2-oxo-1,2-dihydropyridine-3-carboxamide;
N-(3-Fluoro-4-(7-hydroxy-6-methoxyquinolin-4-yloxy) phenyl)-1-(4-fluorophenyl)-2-oxo-1,2-dihydropyridine-3-carboxamide;
N-(3-Fluoro-4-(6-methoxy-7-(piperidin-4-ylmethoxy) quinolin-4-yloxy)phenyl)-1-(4-fluorophenyl)-2-oxo-1,2-dihydropyridine-3-carboxamide;
N-(3-Fluoro-4-(6-methoxy-7-((1-methylpiperidin-4-yl) methoxy)quinolin-4-yloxy)phenyl)-1-(4-fluorophenyl)-2-oxo-1,2-dihydropyridine-3-carboxamide;
N-(4-(6,7-Dimethoxyquinolin-4-yloxy)-3-fluorophenyl)-6-(4-fluorophenyl)picolin-N-oxide-amide; and
5-Benzyl-N-(4-(6,7-dimethoxyquinolin-4-yloxy)-3-fluorophenyl)-4-oxo-1,4-dihydropyridine-3-carboxamide.

* * * * *

UNITED STATES PATENT AND TRADEMARK OFFICE
CERTIFICATE OF CORRECTION

PATENT NO. : 7,732,613 B2  Page 1 of 1
APPLICATION NO. : 11/520520
DATED : June 8, 2010
INVENTOR(S) : Kyoung S. Kim It is certified that error appears in the above-identified patent and that said Letters Patent is hereby corrected as shown below:

Claim 1, column 39, line 9, delete "$NR^{14}R^{15}$" and insert -- $NR^{14}R^{15}$, --, therefor; and Claim 8, column 40, line 20, delete "$OCH_2$piperidine." and insert -- —$OCH_2$piperidine. --, therefor.

Signed and Sealed this

Twenty-third Day of November, 2010

David J. Kappos
*Director of the United States Patent and Trademark Office*